United States Patent
Pakhomov et al.

(10) Patent No.: US 11,351,368 B2
(45) Date of Patent: Jun. 7, 2022

(54) MEGAHERTZ COMPRESSION OF NANOSECOND PULSE BURSTS

(71) Applicant: Old Dominion University Research Foundation, Norfolk, VA (US)

(72) Inventors: Andrei G. Pakhomov, Norfolk, VA (US); Shu Xiao, Norfolk, VA (US); Olga N. Pakhomova, Norfolk, VA (US); Maura Casciola, Norfolk, VA (US)

(73) Assignee: Old Dominion University Research Foundation, Norfolk, VA (US)

( * ) Notice: Subject to any disclaimer, the term of this patent is extended or adjusted under 35 U.S.C. 154(b) by 23 days.

(21) Appl. No.: 16/669,419

(22) Filed: Oct. 30, 2019

(65) Prior Publication Data
US 2020/0147371 A1    May 14, 2020

Related U.S. Application Data

(60) Provisional application No. 62/757,739, filed on Nov. 8, 2018.

(51) Int. Cl.
*A61N 1/36* (2006.01)
*A61N 1/08* (2006.01)
*A61N 1/04* (2006.01)

(52) U.S. Cl.
CPC ....... *A61N 1/36002* (2017.08); *A61N 1/0412* (2013.01); *A61N 1/08* (2013.01); *A61N 1/36034* (2017.08)

(58) Field of Classification Search
CPC ............ A61N 1/36002; A61N 1/36034; A61N 1/0412; A61N 1/08
See application file for complete search history.

(56) References Cited

U.S. PATENT DOCUMENTS

| | | | |
|---|---|---|---|
| 6,326,177 | B1 | 12/2001 | Schoenbach et al. |
| 7,344,533 | B2 | 3/2008 | Pearson et al. |
| 8,000,813 | B2 | 8/2011 | Schoenbach |
| 8,512,334 | B2 | 8/2013 | Nuccitelli et al. |
| 8,612,018 | B2 * | 12/2013 | Gillbe .................. A61N 1/0551 607/72 |
| 8,822,222 | B2 | 9/2014 | Beebe et al. |
| 9,101,764 | B2 | 8/2015 | Nuccitelli et al. |
| 9,724,155 | B2 | 8/2017 | Nuccitelli et al. |
| 2002/0193833 | A1 | 12/2002 | Dimmer et al. |
| 2008/0103529 | A1 | 5/2008 | Schoenbach et al. |

(Continued)

FOREIGN PATENT DOCUMENTS

WO    WO2011/146498 A2    11/2011

OTHER PUBLICATIONS

Pakhomov et al.; Excitation and electroporation by MHz bursts of nanosecond stimuli; Biochemical and biophysical research communications; 518(4); pp. 759-764; Oct. 2019.

(Continued)

*Primary Examiner* — Eric D. Bertram
(74) *Attorney, Agent, or Firm* — Shay Glenn LLP

(57) ABSTRACT

Methods and apparatuses (systems, devices, etc.) for treating biological tissue to evoke one or more desirable biological and/or physiological effects using pulsed electric fields in the sub-microsecond range at very low electric field strength (e.g., less than 1 kV/cm) but at high (e.g., megahertz) frequencies.

25 Claims, 19 Drawing Sheets

(56) References Cited

U.S. PATENT DOCUMENTS

| | | | |
|---|---|---|---|
| 2010/0261994 A1* | 10/2010 | Davalos | A61N 1/0412 600/411 |
| 2011/0092973 A1 | 4/2011 | Nuccitelli et al. | |
| 2011/0106221 A1 | 5/2011 | Neal, II et al. | |
| 2012/0109122 A1 | 5/2012 | Arena et al. | |
| 2014/0121728 A1* | 5/2014 | Dhillon | A61F 7/007 607/62 |
| 2014/0364797 A1 | 12/2014 | Schoenbach et al. | |
| 2015/0201991 A1 | 7/2015 | Zemlin | |
| 2016/0184003 A1* | 6/2016 | Srimathveeravalli | A61B 18/1206 606/39 |
| 2017/0245928 A1 | 8/2017 | Xiao et al. | |
| 2017/0266438 A1* | 9/2017 | Sano | A61B 18/1206 |
| 2018/0078755 A1 | 3/2018 | Kreis et al. | |
| 2018/0161086 A1* | 6/2018 | Davalos | A61B 18/14 |
| 2019/0046791 A1 | 2/2019 | Ebbers et al. | |
| 2019/0054294 A1 | 2/2019 | Pakhomov et al. | |
| 2019/0217080 A1 | 7/2019 | Moss et al. | |

OTHER PUBLICATIONS

Ruzgys et al.; Nanosecond range electric pulse application as a non-viral gene delivery method: proof of concept; Scientific Reports; 8(1); pp. 15502; 8 pages; DOI:10.1038/s41598-018-33912-y; Oct. 19, 2018.

International Search Report and Written Opinion dated May 18, 2020 for PCT/US2019/058847; 14 pages.

Preliminary Report on Patentability dated May 18, 2021 for PCT/US2019/058847; 11 pages.

European Supplemental Search Report dated Nov. 30, 2021 for European Patent Application No. 19882032.6; 8 pages.

* cited by examiner

*100 ns pulse, 100 μs between pulses (10 kHz), approx. 8 μs discharge time*

*100 ns pulse, 5 μs between pulses (200 kHz), approx. 8 μs discharge time*

*100 ns pulse, 1 μs between pulses (1 MHz), approx. 8 μs discharge time*

85 V/cm x
1,000p
3.33 MHz
(200 ns pulse
100 ns gap)

1,000p x 3.33 MHz (200 ns pulse, 100 ns gap)

$Ca^{2+}$ activation in ventricular cardiomyocytes, Fluo4

1,000p x 3.33 MHz (200 ns pulse, 100 ns gap)

$Ca^{2+}$ activation in ventricular cardiomyocytes, Fluo4

1,000p x 3.33 MHz (200 ns pulse, 100 ns gap)
$Ca^{2+}$ activation in ventricular cardiomyocytes, Fluo4

FIG. 11B  FIG. 11C  FIG. 11D

Electroporation of CHO cells by a compressed burst of 300-ns pulses

Electroporation of CHO cells by a compressed burst of 300-ns pulses

MEGAHERTZ COMPRESSION OF NANOSECOND PULSE BURSTS

CROSS REFERENCE TO RELATED APPLICATIONS

This patent claims priority to U.S. provisional patent application No. 62/757,739, titled "MEGAHERTZ COMPRESSION OF NANOSECOND PULSE BURSTS" filed on Nov. 8, 2018, which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

STATEMENT AS TO FEDERALLY SPONSORED RESEARCH

This invention was made with Government support under Grant No. R01HL128381 awarded by the National Institute of Health (NIH/NIHLBI), and Air Force Office of Scientific Research (AFOSR), Grant No. FA9550-15-1-0517. The Government has certain rights in the invention.

FIELD

The apparatuses and methods described herein relate to biological treatment apparatuses and methods for applying a train of nanosecond electrical pulses at low voltage (e.g., <20 V) and high (e.g., megahertz) frequency.

BACKGROUND

Electrical treatment using pulses in the nanosecond range has many applications in medicine, research, and biotechnology. The applications include, for example, electrostimulation and activation of cells and tissues, induction of cell differentiation and death, tumor and tissue ablation, defibrillation, etc. Typically, treatments using electrical pulses in the nanosecond range use high voltages to exceed the local electric field threshold for desired bio-effects. For example, depending on the desired biological effect, the threshold for single nanosecond pulses may be on the order of several kV/cm for a single pulse, which may be larger for shorter pulses. For example, 2.5 kV/cm is a typical threshold for activation of cardiomyocytes by 200-ns pulses; 1.8 kV/cm is a typical threshold for induction of calcium transients in HEK293 cells with 300-ns pulses; 6 kV/cm and 1 kV/cm are typical thresholds for permeabilization of CHO cells by 60- and 600-ns pulses, respectively. Furthermore, delivering multiple nanosecond electric pulses at repetition rates of 1 Hz-1 kHz increases the effect, usually in the additive manner, but without decreasing the threshold electric field, or at best resulting in a modest reduction of the threshold (e.g., 2-3-fold).

It would be desirable to provide electrical pulses to achieve a desired biological effect using nanosecond pulses at low voltages, which may allow safer, and lower-cost treatments.

SUMMARY OF THE DISCLOSURE

Traditionally, sub-microsecond electrical therapies were thought to require a high electric field, typically from 1 to over 50 kV/cm, in order to elicit bioeffects. As described herein, the inventors have found that this requirement can be overcome by engaging temporal summation when pulses are compressed into high-rate bursts, e.g., up to several MHz, using significantly lower electric fields. This technique using intense nanosecond pulsed electric filed (nsPEF) may be used for cell activation, nanoelectroporation and excitation of electrically cells, including in particular nerves such as ventricular cardiomyocytes and peripheral nerve fibers, for membrane electroporation, and/or for killing cells. Megahertz compression of sub-microsecond electrical bursts (100-1000 pulses) enables excitation at significantly lower energy densities (e.g., between about 0.01-0.15 kV/cm), and/or may permit electroporation at lower energy densities (e.g., between about 0.4-0.6 kV/cm) than previously. In some variations, because of the separation of excitation and electroporation thresholds, multiple excitation cycles may be performed without membrane disruption. The efficiency of these sub-microsecond bursts of energy may increase with the duty cycle, e.g., by increasing either pulse duration or repetition rate, and/or may increase by increasing the total time "on", e.g., by increasing either pulse duration or number. In some variations, the efficiency of sub-microsecond bursts of electrical energy may match that of single "long" pulses whose amplitude and duration are approximately equal to the time-average amplitude and duration of the bursts. The use of high frequencies (e.g., 5 kHz or more, 10 kHz or more, 100 kHz of more, 200 kHz or more, 500 kHz or more, 1 MHz or more, etc.) and low electric fields with sub-microsecond electrical bursts may therefore provide an efficient way to lower excitation thresholds and/or to facilitate electroporation.

Thus, described herein are methods and apparatuses (e.g., systems, devices, etc.) that may evoke one or more desirable biological and/or physiological effects using pulsed electric fields in the sub-microsecond range at very low electric field values (e.g., less than 1 kV/cm at the target tissue) but at high (e.g., megahertz) frequencies.

For example, described herein are methods for treating a target region of biological tissue to evoke a biological effect, the method comprising: passing a sub-microsecond pulsed electric field through the biological tissue, wherein the pulsed electric field has an amplitude of less than 1 kV/cm at the target region of the biological tissue and the pulsed electric field is pulsed at equal or greater than 0.1 megahertz (e.g., 0.2 MHz or greater, 0.5 MHz or greater, 1 MHz or greater, etc.). The sub-microsecond pulsed electric field may comprise pulses in nanosecond range, for example, of 1000 ns or less.

The biological effect may be one of: electrical stimulation (e.g., evoking an action potential, activation of voltage-sensitive ion channels, causing an influx in charged ions, depolarizing a cell or cells, etc.), poration, evoking an immune response, transferring material through a cell, etc.

Any appropriate biological tissue may be targeted, including any one or more of: skin, liver, kidney, neuronal, brain, spine, lung, muscle, adipose, respiratory, gastrointestinal, bladder, and reproductive. In particular, the tissue may be disease tissue, including but not limited to cancer.

Also described herein are apparatuses (e.g., systems) for treating a biological tissue, which are configured to perform any of the methods described herein. For example, the system may include: a controller; an applicator comprising a set of electrodes adapted to be placed in proximity to the biological tissue; and one or more pulse generator, wherein each pulse generator is configured to generate a sub-microsecond pulse (e.g., having a duration of 1000 ns or less);

wherein the controller is configured to apply a train of sub-microsecond pulses at a frequency of greater than 0.1 megahertz (e.g., 0.2 MHz or greater, 0.5 MHz or greater, 1 MHz or greater, etc.). The system may be configured to generate an electric field strength of less than 1 kV/cm, for example, between 0.01 and 0.15 kV/cm, or less than 0.6 kV/cm. The amplitude of the voltage applied by the applicator may be equal or less than 20 V. The controller may be configured to coordinate the plurality of pulse generators to combine nanosecond pulses from each of the plurality of pulse generators.

For example, a system for treating a biological tissue may include: a plurality of pulse generators; and a controller comprising one or more processors, the controller including a machine-readable tangible medium storing instructions for causing the one or more processors to execute operations for: passing a nanosecond pulsed electric field through the biological tissue, wherein the pulsed electric field has an amplitude of less than 1 kV/cm, wherein the pulsed electric field is pulsed at equal or greater than 0.1 megahertz (e.g., 0.2 MHz or greater, 0.5 MHz or greater, 1 MHz or greater, etc.).

Also described herein are methods of evoking a biological effect in a target region of tissue where multiple, spatially separate source of pulse electrical energy are concurrently driven to apply pulsed (e.g., sub-microsecond pulses) of electrical energy to the tissue. For example, a method for treating a biological tissue to evoke a biological effect may include: delivering a first nanosecond pulsed electric field to a target region, wherein each pulse of the first nanosecond pulsed electric field is equal or less than 1 microsecond duration; delivering, concurrent with the first nanosecond pulsed electric field, a second nanosecond pulsed electric to the target region, wherein each pulse of the second nanosecond pulsed electric field is equal or less than 1 microsecond duration; and forming a summed pulsed electric field in the target region, the summed pulsed electric field comprising a superposition of the first and second nanosecond pulsed electric filed and having an amplitude of less than 1 kV/cm, wherein the summed pulsed electric field comprises pulses having a pulsing frequency equal or greater than 0.1 megahertz (e.g., 0.2 MHz or greater, 0.5 MHz or greater, 1 MHz or greater, etc.).

Also described herein are methods of operation of a pulse generator. In some embodiments, the method comprises generating a high-frequency, sub-microsecond pulsed electric field, wherein the high-frequency, sub-microsecond pulsed electric field has a field strength of less than 1 kV/cm, a frequency of 0.1 megahertz or greater (e.g., 0.2 MHz or greater, 0.5 MHz or greater, 1 MHz or greater, etc.) and wherein each pulse has a duration of less than 1000 ns. In some embodiments, the method of operation of one or more pulse generators comprises delivering a first nanosecond pulsed electric field, wherein each pulse is less than 1 microsecond in duration; delivering, concurrent with the first nanosecond pulsed electric field, a second nanosecond pulsed electric field, wherein each pulse is less than 1 microsecond in duration; and summing the first and the second pulsed electric field to deliver a high-frequency, sub-microsecond pulsed electric field comprising a superposition of the first and the second sub-microsecond pulsed electric fields having a field strength of less than 1 kV/cm and a frequency of 0.1 MHz or greater (e.g., 0.5 MHz or greater, 1 MHz or greater, etc.).

In any of these methods at least one of the first and second nanosecond pulsed electric field may comprise bipolar pulses (and preferably both), which may reduce effects near the sources (e.g., electrodes, antenna, etc.) of the emitted electric fields.

Also described herein are systems for treating a biological tissue that may include: a plurality of pulse generators; and a controller comprising one or more processors, the controller including a machine-readable tangible medium storing instructions for causing the one or more processors to execute operations for: passing a first nanosecond pulsed electric field through the biological tissue to a target region, wherein each pulse of the first nanosecond pulsed electric field is equal or less than 1000 ns duration; passing, concurrent with the first nanosecond pulsed electric field, a second nanosecond pulsed electric field through the biological tissue to the target region, wherein each pulse of the second nanosecond pulsed electric field is equal or less than 1000 ns duration; and forming a summed pulsed electric field in the target region, the summed pulsed electric field comprising a superposition of the first and second nanosecond pulsed electric filed and having an amplitude of less than 1 kV/cm, wherein the summed pulsed electric field comprises monopolar pulses having a pulsing frequency equal or greater than 0.1 megahertz, further wherein each pulse is equal or less than 1000 ns duration.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 4B is an example of a schematic for an apparatus for applying nanosecond electrical pulses at low electric field and high (e.g., megahertz) frequency, including a plurality of pulse generators that may be controlled by a controller to deliver a train of nanosecond pulses that are separated less than 1000 ns (e.g., having a frequency of greater than or equal to 0.1 MHz,).

FIG. 4C is an example of a train of nanoseconds formed by a device such as the one shown in FIG. 4B; in FIG. 4C, the pulse generator (from FIG. 4B) responsible for generating each pulse in the train of pulses is indicated.

In FIG. 5, the pulse generator may be used to generate bipolar pulses.

In FIG. 8A a pulse train of 200 ns pulses at 3.33 MHz (separated by 100 ns between pulses) was applied at 10 s. FIG. 8A shows a time lapse recording of calcium activation (Fluo-4 dye emission, left column) and resulting cell contraction (DIC, right column). Images were taken with 0.24 s intervals, from top to bottom. Next images taken in the same experiment (up to 48 s, not shown) reveal no additional changes. Burst parameters and the onset of burst delivery (arrow) are indicated.

In FIG. 8B, a train of nanosecond electrical pulses was applied to a mouse ventricular cell; the pulse train of 200 ns pulses was applied at 3.33 MHz (separated by 100 ns between pulses) at the 10 second time point. FIG. 8B shows selected time lapse of irreversible cell membrane damage and cell reshaping resulting from a higher amplitude burst. The time when each pair of images was taken is indicated at the right side of the figure.

FIGS. 11B-11E illustrate action potential thresholds for isolated ventricular cardiomyocytes (VCM) measured with FluoVolt dye. FIG. 11B is a graph showing the effect of pulse number for bursts of 100-, 200-, or 400-ns pulses, all with 100-ns interval, showing that increasing the number of pulses decreased the threshold similarly for all durations. FIG. 11C is a graph showing the thresholds plotted against the total time "on" did not depend on pulse duration. FIG. 11D is a graph showing bursts of shorter high frequency, sub-microsecond, low electric field pulse excited VCM at lower time-average electric field. For all of FIGS. 11B-11D, Mean±s.e., n=6-10.

FIG. 11E is a graph showing the same result as in FIG. 11D for bursts of 1000 pulses, 50- to 600-ns duration. Interpulse intervals were varied from 0.09 to 4.8 μs. Mean±s.e., n=25-30.

FIG. 12A shows electroporation of CHO cells by a compressed train (e.g., a burst) of 300-ns pulses, and specifically, the time course of cytosolic Ca2+ response in a representative group of 8 CHO cells following the burst (arrow). Solid black lines are the data from individual cells, and the curve with points is their mean value+/−s.e.

FIG. 13 (bottom) shows $Ca^{2+}$ activation by bi and monopolar nanosecond pulses in CHO cells (mean +/−s.e., n=20-28). The top of FIG. 13 shows bipolar and monophasic pulse shapes and amplitudes.

In FIGS. 16B-16D, mean±s.e., n=5-9, and data collected using isolated frog sciatic nerves.

FIG. 17A is a graph showing that (in CHO cells) 100-pulse, 400-ns bursts become increasingly more efficient above 0.1-0.3 MHz. Labels indicate the electric field, in kV/cm; 20-30 cells per data point. FIG. 17B is a graph showing the time course of YO-PRO-1 uptake (in HEK cells) evoked by 1000 of 500-ns, 0.64 kV/cm pulses (arrow) at indicated duty cycle. FIG. 17C is a graph showing the last data point from FIG. 17B plotted against the repetition rate, showing a lack of effect below 1 MHz. FIG. 17D is a graph showing $Ca^{2+}$ transients evoked by same bursts (arrow) in HEK cells. FIG. 17E is a graph showing similar $Ca^{2+}$ transients evoked by one 500-µs pulse at indicated electric fields. FIG. 17F shows maximum amplitude of $Ca^{2+}$ transients from the graphs of FIGS. 17D and 17E plotted against the electric field for a single 500-µs pulse (and against the duty cycle for high frequency, sub-microsecond, low electric field bursts). Mean±s.e., n=11-27 for all panels. HEK cells were stimulated in a low-conductance solution.

FIG. 18A illustrates the shape of high frequency, sub-microsecond, low electric field pulses delivered to electroporation cuvettes. The dashed line denotes the time-average amplitude. FIG. 18B illustrates the effect of pulse number for 100-Hz and 3-MHz bursts for a low electric field of about 1.9 kV/cm. FIG. 18C is a graph showing the same dependence for a high electric field of 5 kV/cm. FIG. 18D is a bar chart illustrating the high frequency, sub-microsecond, low electric field bursts at indicated parameters kill about 50% of cells, whereas a single pulse (whose duration equals burst duration and the amplitude equals the average of the burst) has smaller effect. Mean±s.e., n=5-6. *p<0.0001, t-test.

DETAILED DESCRIPTION

Figure 1:
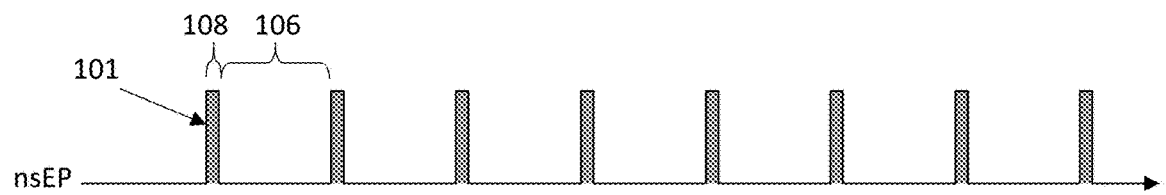
FIG. 1 is an example of a train of sub-microsecond (e.g., nanosecond) electrical pulses as described herein, having a low peak voltage (e.g., less than 20 V), and a high frequency (e.g., megahertz) between pulses (e.g., having intervals between sequential nanosecond pulses that are typically less than 500 ns). The methods and apparatuses described herein refer to sub-microsecond pulses, which generally include pulses having duration of about equal or less than 1 microsecond, but in some variations may include pulses of 10 μs or less (e.g., 10000 ns or less). For example, in some applications sub-microsecond pulses may each be between 0.1 ns and 1000 ns (e.g., between 50-500 ns, between 100-400 ns, etc.).

Described herein are methods and apparatuses (systems, devices, etc.) that may evoke one or more desirable biological and/or physiological effects using electrical pulses in the sub-microsecond (e.g., nanosecond) range at 0.1 megahertz and above (MHz) frequencies, which may permit the use of substantially lower electric fields compared to other techniques. For convenience, this electrical pulsing according to the present disclosure may be referred to as megahertz compression, megahertz compression of nanosecond pulses, or megahertz compression of nanosecond pulse trains (e.g., bursts). Unlike traditional nanosecond pulsed electric field treatments, which typically refers to very short, high intensity pulses (e.g., high electric field, typically much larger than 1 kV/cm), megahertz compression of nanosecond pulses may use much lower intensities, e.g., reduction by 5- to 10-fold or greater. For example, megahertz compression of nanosecond pulses may use very low electrical filed values (e.g., at the target site) that are less than 1 kV/cm (e.g., less than 900 V/cm, less than 800 V/cm, less than 750 V/cm, less than 700 V/cm, less than 600 V/cm, less than 500 V/cm, etc.), which is made possible by applying the nanosecond electrical pulses at very fast rates, e.g., in the megahertz (MHz) range. The megahertz range may include 0.1 MHz or greater (e.g., 0.2 MHz or greater, 0.4 MHz or great, 0.5 MHz or greater, 0.7 MHz or greater, 1 MHz or greater, etc.) Surprisingly, the apparatuses and methods described herein have been shown to result in biological efficiency of nanosecond electrical pulses to induce bioeffects at very low electric field values; specifically, at field values that were previously believed to have no effect. The apparatuses described herein are specifically configured to deliver pulse trains (e.g., bursts) of low-amplitude nanosecond electrical pulses in the megahertz range, e.g., having intervals between sequential nanosecond electrical pulses that are typically equal or less than 1 microsecond (e.g., less than about 900 ns, less than about 800 ns, less than about 700 ns, less than about 600 ns, less than about 500 ns, less than 450 ns, less than 400 ns, less than 350 ns, less than 300 ns, etc.).

As mentioned above, traditional high-intensity, sub-microsecond pulsing has been limited to high pulse voltages in order to exceed the electric field (EF) threshold for short pulse durations (e.g., when applying sub-microsecond pulsing). This threshold increases with pulse shortening, up to tens of kV/cm. Strength-duration curves for neurostimulation within the nanosecond range typically require thresholds of between about 1 and 240 kV/cm for 100- and 1-ns pulses, respectively. For example, reported thresholds for a single high intensity, sub-microsecond pulsed electric field stimulus include between 1.4-2.4 kV/cm (e.g., for activation of cardiomyocytes by 200 ns pulses), greater than 1.8 kV/cm (e.g., for induction of calcium transients in HEK293 cells with 300-ns pulses), between 6 kV/cm and 1 kV/cm (e.g., for permeabilization of CHO cells by 60- and 600-ns pulses). Thus, it has long been believe that pulse voltages required to reach these thresholds were prohibitively high. For example, achieving 10 kV/cm to ablate a tumor between two parallel-plate electrodes with a 2-cm gap typically requires 20 kV applied to the electrodes. Such voltages are beyond the capability of most pulsed generators and may present a high-voltage hazard. The methods and apparatuses described herein may avoid these problems.

For example, the methods an apparatuses descried herein may use lower electric field intensities, while providing comparable or superior effects. For example, the methods and apparatuses described herein may be used where high intensity, sub-microsecond pulsed electric fields have previously been shown to be effectively used, for example, for neuromuscular stimulation, including activating ion-selective nanopores (e.g., mobilization of cytosolic $Ca^{2+}$ in both excitable and non-excitable cells, and opening inwardly rectifying and ion-selective stable nanopores in cell membrane), to cause non-chemical activation of diverse cell and tissue types and, at higher doses, to provide highly selective cell killing by necrotic and/or apoptotic pathways. The methods and apparatuses described herein may therefore also be used for defibrillation, peripheral nerve and deep brain stimulation, and tissue or cell ablation (e.g., cancer ablation).

Delivering multiple stimuli can result in a stepwise voltage build-up on the membrane of the target cell, eventually reaching the excitation or electroporation threshold when the interpulse interval is shorter than the relaxation of the induced transmembrane potential. Charging time constants in mammalian cells are typically at 0.1-1 µs. Temporal summation can only be expected at interpulse intervals smaller than 3-5 time constants (which correspond to 95 and 99% discharge between sequential pulses), which translates into repetition rates from tens of kHz to more than 1 MHz. As described herein, delivering multiple sub-microsecond pulsed electrical energy at repetition rates of 1 Hz-5 kHz may cause stronger effects than a single pulse, but either without decreasing the threshold, or with a modest reduction of the threshold.

For example, described herein is MHz compression of sub-microsecond electrical pulse bursts that facilitates excitation and electroporation at electric field levels of, e.g., between 10-150 V/cm. As described, the efficiency may depend on the pulse and burst parameters, which also differ from conventional ("long") sub-microsecond electric stimuli.

FIG. 1 illustrates one example of a nanosecond pulse train (e.g., a nanosecond electrical pulse train) applied at low voltage (or low electrical density, in V/cm) and high, e.g., megahertz, frequency. In FIG. 1, the pulse train may include a plurality of nanosecond pulses 101, each having a duration within the nanosecond range 108 (e.g., between about 0.1 ns duration and 1000 ns, e.g., between about 0.1 ns and about 950 ns, between about 1 ns and about 900 ns, between about 1 ns and about 800 ns, between about 1 ns and about 750 ns, between about 1 ns and about 700 ns, between about 1 ns and about 600 ns, less than about 1000 ns, less than about 900 ns, less than about 800 ns, less than about 750 ns, less than about 600 ns, less than about 500 ns, etc.). The nanosecond pulses may be separated by a pulse interval 106 of less than about 1000 ns, less than about 900 ns, less than about 800 ns, less than about 750 ns, less than about 700 ns, less than about 600 ns, less than about 500 ns, etc. Thus, the frequency of the nanosecond electrical pulses may be in the megahertz range, such as between about 0.1 MHz and about 50 MHz, between about 0.1 MHz and about 40 MHz, between about 0.1 MHz and about 30 MHz, between about 0.1 MHz and about 25 MHz, between about 0.1 MHz and about 20 MHz, between about 1 MHz and about 50 MHz, between about 1 MHz and about 40 MHz, between about 1 MHz and about 30 MHz, between about 1 MHz and about 25 MHz, between about 1 MHz and about 20 MHz, greater than 0.1 MHz, greater than 0.2 MHz, greater than 0.5 MHz, greater than 0.1 MHz, greater than 1.5 MHz, greater than 2 MHz, greater than 2.5 MHz, etc.

The energy applied by the nanosecond pulses of a pulse train such as the one shown in FIG. 1 may be relatively low. For example, the peak voltage applied by each nanosecond pulse may be less than about 500 V, less than about 100 V, less than about 50 V, less than about 40 V, less than about 30 V, less than about 25 V, less than about 20 V, between about 0.5 V and 50 V, between about 1 V and 25 V, etc. Similarly the resulting electric field of the applied nanosecond pulses (e.g., at the tissue) may be, e.g., less than about 1000 V/cm, less than about 900 V/cm, less than about 800 V/cm, less than about 700 V/cm, less than about 600 V/cm, less than about 550 V/cm, between about 1 V/cm and about 1000 V/cm, between about 10 V/cm and 900 V/cm, etc.

In general, megahertz compression of nanosecond pulses may be applied to a biological cell and/or tissue either directly or indirectly. For example, the application may be made into a patient's body via one or more tissue penetrating electrodes, and/or via surface electrodes. In some variations electrical stimulation using megahertz compression of nanosecond pulses may be applied to isolated cells and/or isolated tissues.

Without being bound by any particular theory of action, it is possible that the application of nanosecond pulses using megahertz compression of nanosecond pulses may allow the applied electrical energy to accumulate in the target cell or cell region, allowing multiple small-amplitude (e.g., less than about 500 V, less than about 100 V, less than about 50 V less than about 40 V, less than about 30 V, less than about 20 V, between about 0.1 V and 50 V, between about 1 V and 30 V, between about 1 V and 20 V, etc.) pulses to sum to a level that exceeds the threshold for a biological effect. For example, nanosecond electrical pulses applied in the megahertz range at frequency that is shorter than the effective electrical discharge time of living cells may result in summing of the charge to above the threshold for a desired effect. For different mammalian cells, the discharge time constant (τ) of the cell (e.g., of the cell membrane) typically varies from about 100 ns for small cells, to about 1 microsecond for larger cells (and may be even longer for cells tightly packed in a tissue), thus the induced membrane potential reduces to approximately 37%, 15%, and 5%, 2% when the discharge duration equals 1τ, 2τ, 3τ, and 4τ, respectively. It is possible that when nanosecond electrical pulses are applied in a pulse train at a rate that is greater than the discharge rate (e.g., when the membrane is not fully discharged), the induced potential may add upon the remaining potential. With multiple pulses all applied with short enough inter-pulse intervals, the induced membrane potential can gradually climb up and exceed the threshold potential to induce bio-effects. See, e.g., FIGS. 2A-2C. For example, if one assumes that 4τ is the longest time interval between the pulses to enable temporal summation of induced potentials, the interpulse intervals may not exceed 400 ns for smaller cells and 2,500 ns for large cells (perhaps up to 10,000 for still larger cells with irregular shape. Shorter inter-pulse intervals may allow faster accumulation of the threshold transmembrane potential. In practice, this means that nanosecond electrical pulse trains may be compressed to deliver the stimuli at repetition rates as high as 0.1-2 MHz, with still higher rates (up to 1,000 MHz) useful to further reduce the amplitude thresholds for shorter nanosecond electrical pulses and smaller cells.

Figure 2A:
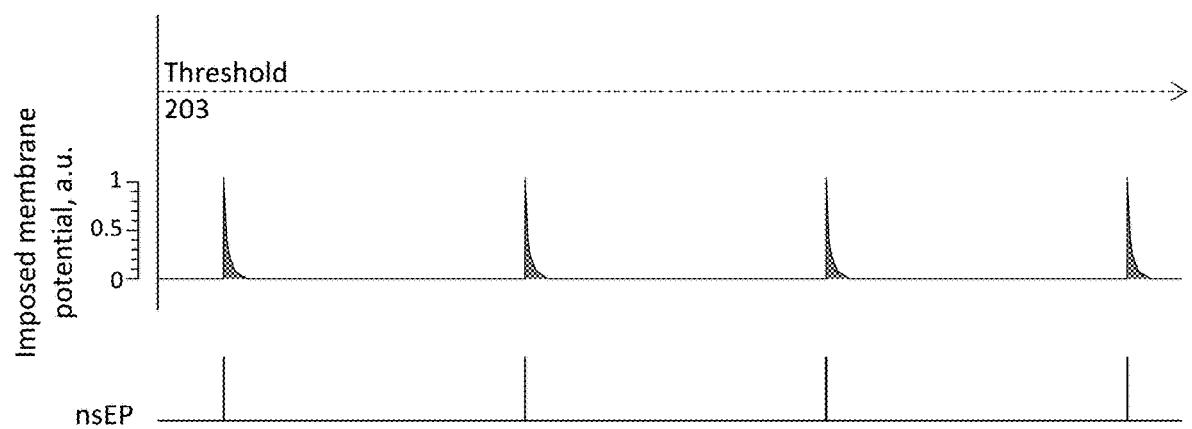
FIG. 2A is an example showing a train of 100 ns pulses (bottom) at a 10 kHz frequency, e.g., having a 100 μs interval between pulses. Each pulse evokes an increase in transmembrane potential in a cell, shown in the upper trace in arbitrary units, and a discharge; in this example, the cells have an 8 μs discharge time. A threshold level is shown by the dashed line at the top.

In the example of FIG. 2A, nanosecond pulses are applied to a cell or tissue in a pulse train at a frequency of 10 kHz (e.g., separated by about 100 μs between each pulse). Individual pulses are 10 ns in duration, as shown on the bottom trace. The upper trace shows the imposed membrane potential (in arbitrary units) resulting from each pulse. For this example tissue or cell, the discharge time is approximately 8 μs. The horizontal dashed line 203 represents the minimum threshold for a biological effect (e.g., stimulation, poration, etc.) that may be triggered when the electrical potential of the membrane (which may include the outer cell membrane and/or one or more internal cell membranes) reaches the threshold. The tissue or cell may have multiple thresholds, corresponding to different or increasing effects.

Figure 2B:
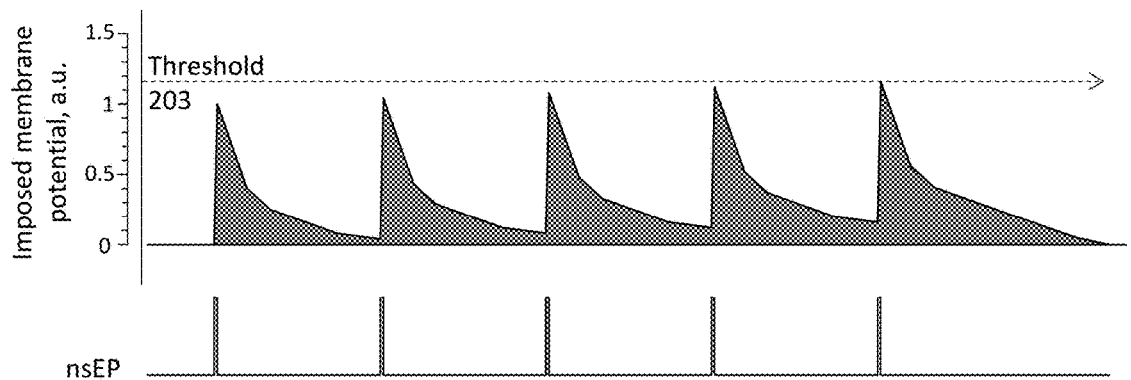
FIG. 2B is similar to FIG. 2A, but pulsing at a frequency of 200 kHz, or 5 μs between each pulse.
Figure 2C:
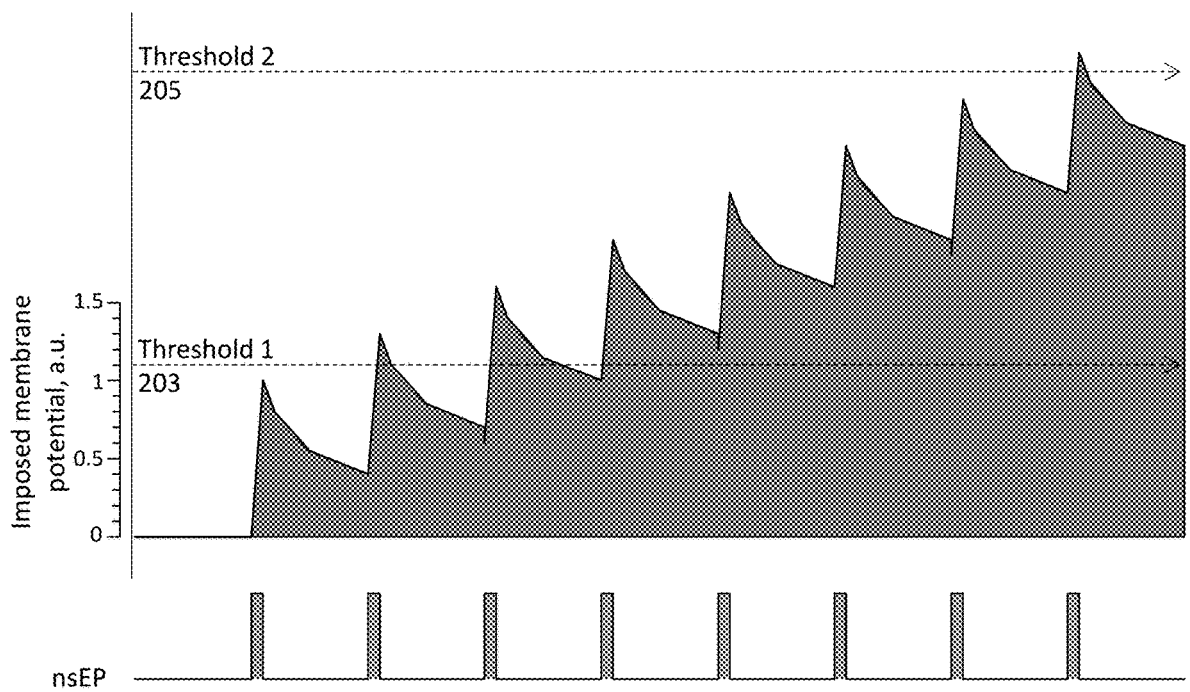
FIG. 2C is similar to FIGS. 2A and 2B, but pulsing at a frequency of 1 MHz, or 1 μs between each pulse. As shown, at this frequency the cell membrane does not fully discharge before the next nanosecond pulse, resulting in the membrane potential exceeding the threshold (threshold 1) after just a few pulses and approaching an exceeding a second threshold (threshold 2) after additional pulsing.

FIGS. 2B and 2C illustrate megahertz compression of nanosecond pulse bursts, showing that megahertz compression permits the cell or tissue to reach and exceed one or more thresholds for bio-effects without increasing pulse amplitude. For example, in FIG. 2B, each 100-ns pulse (bottom trace) induces a transmembrane potential (upper trace, in arbitrary units). Because the energy is not discharged as quickly as the inter-pulse interval, it accumulates, until the continued application of nanosecond pulses causes the imposed membrane potential to exceed the threshold 203, as shown, which may result in the corresponding bio-effect. In FIG. 2B, the marginally high rate (e.g., 100 ns pulses with approximately 5 us between each pulse) results in a minor temporal summation which helps to reach the low threshold 203 that may induce some bio-effect. In FIG. 2C, when a high repetition rate (e.g., 1 MHz, with 1 us between pulses) is applied, the imposed membrane potential may accumulate faster and reach a much higher threshold 205.

System for the Application of Megahertz Compression of Nanosecond Pulses

Figure 3:
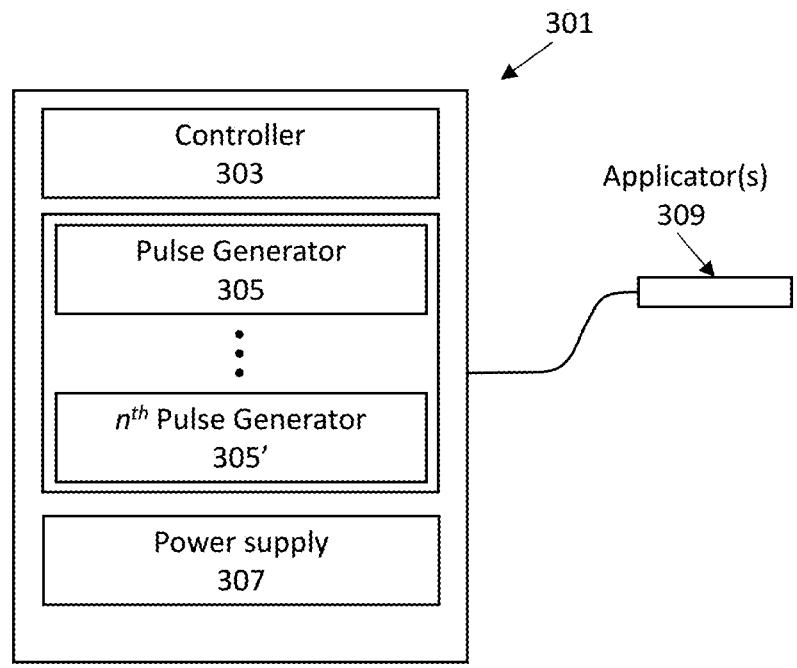
FIG. 3 is a schematic illustration of one example of an apparatus for applying electric pulses in the nanosecond range at low energy (e.g., low electric field) and high frequency (e.g., in the megahertz range). For example, the apparatus may be configured to include a controller controlling a power supply and one or a plurality of nanosecond pulse generators configured to apply pulses having a pulse width of between about 0.1 ns and 1000 ns, an amplitude of between 0.1 V and 20 V and a frequency of between 0.1 MHz and 30 MHz.
Figure 4A:
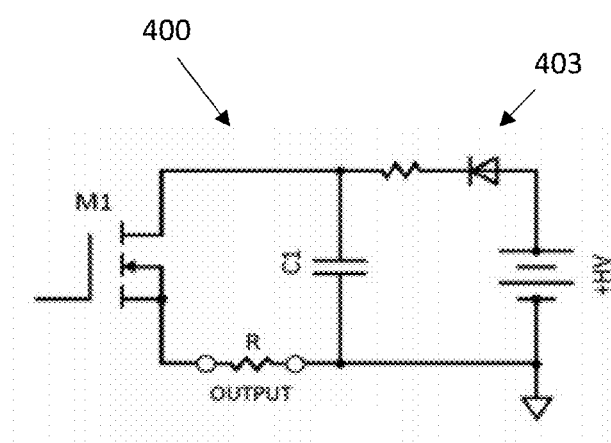
FIG. 4A illustrates one example of a circuit schematic for a pulse generator for a device such as the one shown in FIG. 3.
Figure 5:
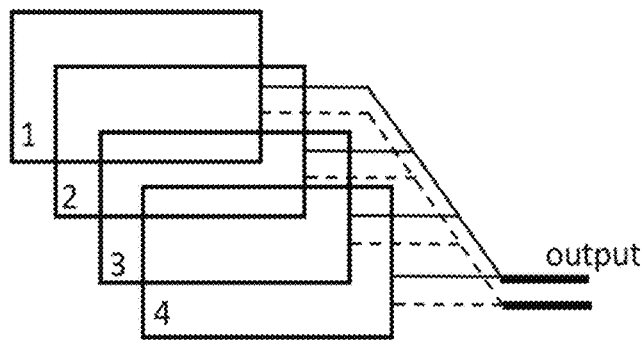
FIG. 5 is another example of a pulse generator apparatus configured to generate nanosecond pulses at low electric field and high (e.g., megahertz) frequency.
Figure 5:
Figure 5:
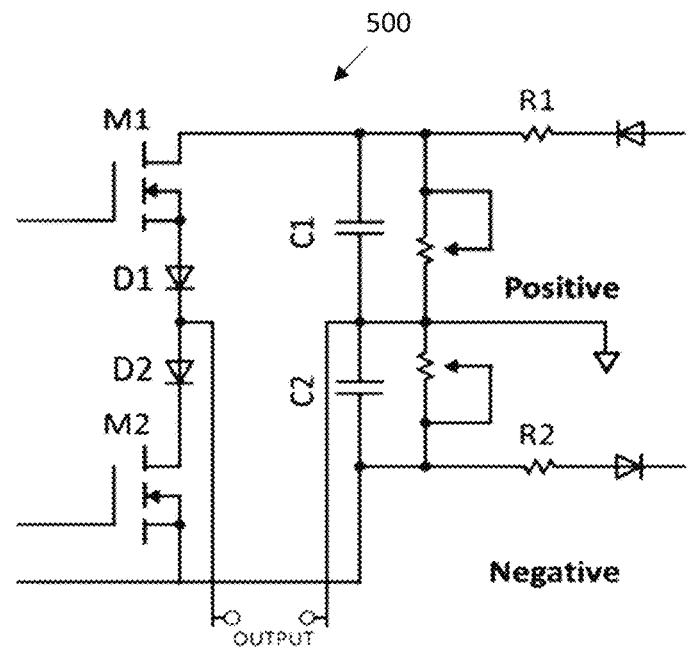

FIGS. 3-5 illustrate examples of systems that may be used to provide megahertz compression of nanosecond pulses. For example, FIG. 3 is a schematic of one example of a system 301 for applying nanosecond pulsing using megahertz compression of nanosecond pulses. In FIG. 3, the system may include at least a controller 303, one or more pulse generators 305, a power supply, and one or more applicators 309. The system may be portable, and the power source may include power conditioning circuitry that receives power from a battery and/or a wall source (e.g., outlet). The battery may be rechargeable. The system may be at least partially enclosed. In some variations the applicator may be connected via one or more cables. Alternatively, the applicator may be integrated with the rest of the system in a compact, hand-held configuration.

The controller may be configured to apply a fixed or adjustable train of nanosecond pulses in which the individual pulses are separated by a fixed or adjustable inter-pulse interval so that the frequency is in the megahertz range (e.g., between about 0.9 MHz and 100 MHz). The inter-pulse interval may be between, e.g., 1200 ns and 50 ns (e.g., within the megahertz frequency range), such as between about 1000 ns and 50 ns, between about 1000 ns and 75 ns, between about 1000 ns and 80 ns, between about 1000 ns and 90 ns, between about 1000 ns and 100 ns, etc. In some variations the controller is configured or adapted to limit the applied stimulation to within this frequency range; in some variations the apparatus may include one or more user inputs (knobs, dials, touchscreens, etc.) in communication with the controller to allow the user to adjust the applied frequency/inter-pulse interval within this megahertz range. Alternatively or additionally, the controller may be configured to allow the user to adjust the number of pulses, the duration that pulses will be applied, and/or voltage applied. The voltage applied may typically be within a predetermined range (e.g., voltage amplitude of between about 0.1 V and about 50 V, between about 0.1 V and 40 V, between about 0.5 V and 30 V, between about 1 V and about 20 V, less than about 50, less than about 40 V, less than about 30 V, less than about 25 V, less than about 20 V, etc.). In some variations, the intensity of the electric field may be selected (e.g., between about 1 V/cm and about 900 V/cm, between about 1 V/cm and about 800 V/cm, between about 10 V/cm and about 750 V/cm, between about 10 V/cm and about 700 V/cm, between about 50 V/cm and about 650 V/cm, less than 1000 V/cm, less than 900 V/cm, less than 800 V/cm, less than 750 V/cm, less than 700 V/cm, less than 600 V/cm, less than 500 V/cm, etc.). Any of these ranges may be considered within the low-voltage range. As mentioned, in some variations the controller may allow the user (e.g., doctor, surgeon, technician, etc.) to select from a predetermined set of values or range, including any of the ranges described herein. In some variations the user may be provided with preset values for one or more of: number of pulses, pulse duration (within the nanosecond range), pulse amplitude (e.g., peak voltage within the predetermined low-voltage range), inter-pulse interval and/or frequency (e.g., within the megahertz range), etc. In some variation the apparatus may be preset or may automatically select appropriate parameters, and the user may only select start or stop, or may select between a limited number of parameter states.

The controller may include hardware, software and/or firmware to allow it to control the operation of the system and/or receive controlling input from the user. For example, the controller may include circuitry including one or more processors, one or more timing circuits, one or more memories, etc. As mentioned, the system may include one or more inputs (e.g., controls) and/or may receive input from another device (e.g., via a wired or wireless connection). The system may include one or more outputs (e.g., monitors, displays, LEDs, etc.), including indicators of the device operation (e.g., ready, standby, etc.) and/or the settings (number of pules, frequency, voltage amplitude, etc.).

As mentioned, any of the systems described herein may include one or more applicators. An applicator may include two or more electrodes, including arrays of electrodes. The electrodes may be tissue penetrating or non-tissue penetrating. For example, a tissue penetrating electrode may be a needle electrode; a non-tissue penetrating may be a surface electrode or electrodes.

In any of the apparatuses described herein, the controller may coordinate the activation of one or more (e.g., a plurality) of pulse generators, as shown in FIG. 3. Each of the n pulse generators may be configured to apply a nanosecond pulse at a coordinated time, and these pulses may be combined into a single stimulation. The individual please generators may be configured to deliver a pulse having a pulse duration in the nanosecond range (e.g., between about 0.1 ns and about 1000 ns), at a peak voltage within a low-voltage range as described above. While FIG. 3 illustrates a plurality of pulse generators, it should be understood that in various applications only one pulse generator may be used.

For example, FIG. 4A schematically illustrates an example of a pulse generator circuit that may be used. In FIG. 4A, the circuit 400 includes a pre-charged capacitor (C1) switched by an N-type (n-channel) MOSFET switch (M1). The switch may be triggered by one or more low voltage MOSFET drivers. In this example, a Zener diode 403 may be placed at the transformer output to clamp the voltage. The output voltage may be set (e.g., within the low-voltage range described above). The settings may be modified by selecting the R, L, and C and values, creating a critical damped mode that is favorable for ultrafast pulsing.

As illustrated in FIG. 4B, in some embodiments a plurality of pulse generator circuits, such as the pulse generator circuit schematically shown in FIG. 4A, may be coupled together and controlled by the controller, as mentioned above. In FIG. 4B, each block (1, 2, 3, and 4) represents a pulse generator that may be controlled by the controller and used to form a compound/combined nanosecond pulse train of pulses within the megahertz pulsing frequency having a low electric field (e.g., low voltage range). In FIG. 4B, a single pulse generator does not need to generate nanosecond duration pulses at high frequency (e.g., within the multi-MHz range); instead several of the pulse generators are grouped to produce pulses. When using relatively low voltages (e.g., <1 kV, including the low voltage ranges described above) in the pulse regime, the RC-switch modules can be combined laterally to produce multiphasic pulses of arbitrary amplitudes, width and intervals. Each module can be charged with different DC sources, therefore offering different output voltages. Each module can be triggered separately, allowing various pulse widths (PWs) and delays. Alternatively, all or some of the modules may produce identical pulses, which may be combined as described above. FIG. 4C illustrates one example of a combined train of nanosecond-duration pulses originating from four separate but linked pulse generators, such as shown in FIG. 4B. In this example the pulses are nonpolar (e.g., all positive or all negative going) and are shown as equivalent pulses; as mentioned, in some variations pulses having different durations and/or different voltages may be applied within the same pulse train. In some variations, as will be described in greater detail below, bipolar pulses of nanosecond duration may be delivered in the megahertz frequency range.

For example, FIG. 5 illustrate another example of a schematic for a pulse generator configured to provide bipolar stimulation. In FIG. 5 the pulse generator 500 combined positive pulsing circuitry and negative pulsing circuitry to create the bipolar pulse generator. In FIG. 5, the switch connection in the negative pulsing circuitry is drain-to-ground (and source-to-negative) charging, which is opposite to that shown in the positive pulsing circuitry. The same load resistor may be used for both positive and negative pulsing circuitry. The voltage and pulse duration can be differentially adjusted. One can also trigger just one of the positive or negative pulsing circuitry so that either a positive or negative pulse is delivered. A delay of any length can be inserted in any interval. A plurality of bipolar stimulators such as those shown in FIG. 5 may be combined as shown in FIG. 4B, allowing megahertz frequency stimulation. The pulse generators shown in FIGS. 4A-5B represent merely non-limiting examples of pulse generators that may be used to perform the methods described herein. Other pulse generators may be used or configured to generate trains of nanosecond pulses at the described frequencies.

Figure 6:
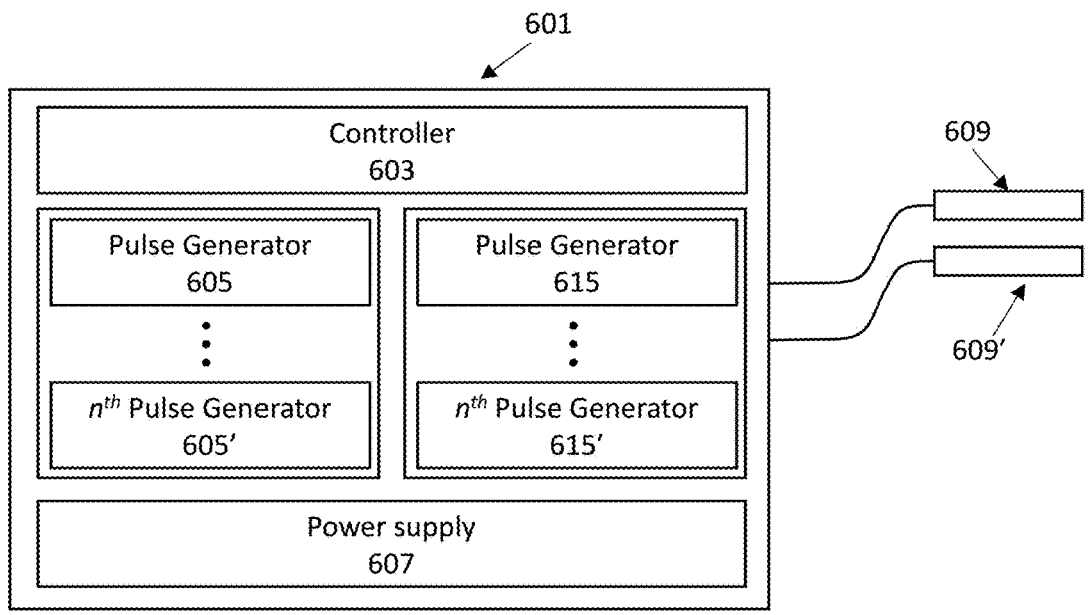
FIG. 6 is a schematic illustration of another variation of a pulse generator apparatus (e.g., system) configured to control and/or coordinate the application of spatially separated nanosecond pulses at low voltage in the megahertz range (e.g., from different applicators and/or different electrodes of a uniform applicator). This applicator may be particularly useful with bipolar nanosecond pulsing, as described herein.

Any of the systems described herein may also be configured as shown in FIG. 6, in which a single controller controls two or more sets of pulse generators that may be used to apply nanosecond electrical pulses from different locations (e.g., on or in a body). In FIG. 6 the system 601 includes a single controller 603 (which, in some variations may be two or more linked controllers) controls and coordinates electrical stimulation by the application of nanosecond pulses at low voltage in the megahertz frequency range from each of two (or two sets) of pulse generators 605 . . . 605' and 615 . . . 615'. As will be described in greater detail below in the context of bipolar pulsing, this may allow for non-invasive electrical stimulation with minimum near-electrode effects. The same power supply 607 or different power supplies may be used to provide power (e.g. to the pulse generators). One or more applicators 609, 609' each including electrodes for the application of the nanosecond pulses may be used. In some variations a single applicator having different electrode sets, which may be separated by a known or predetermined distance and/or geometry, may be used. In one variation of the example shown in FIG. 7, at about 140 um between the tips of the electrodes, pules applying about 16 V was equivalent to about 570 V/cm.

Figure 7:
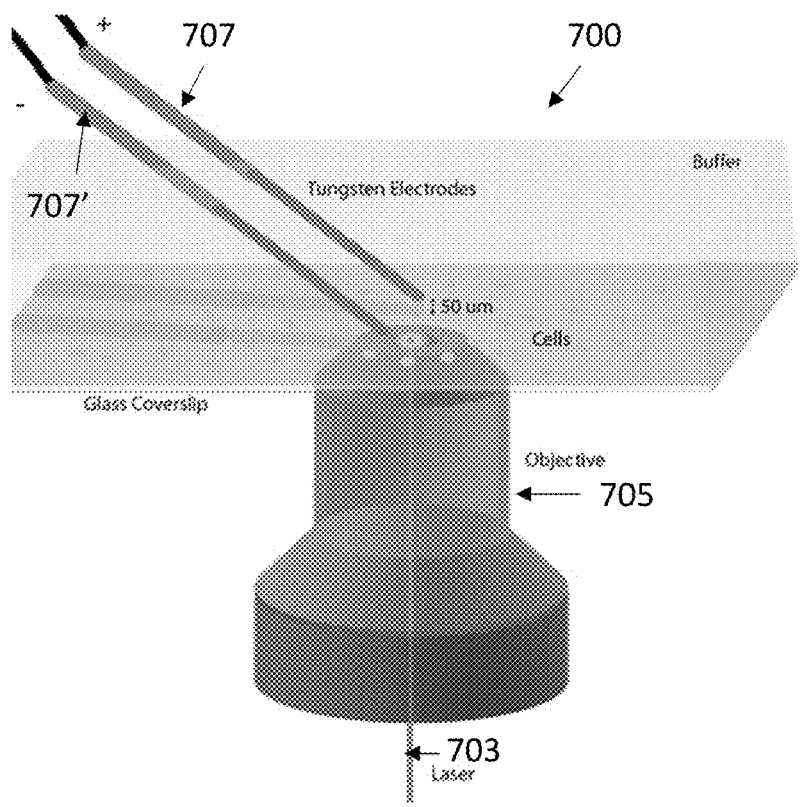
FIG. 7 is an example of an experimental setup to apply nanosecond pulses at low electric field and megahertz frequency to cells. The setup in FIG. 7 also allows imaging of the cells.

The application of megahertz compression of nanosecond pulse bursts, in which low-voltage nanosecond pulses were applied at high (e.g., megahertz) frequencies was examined using an in vitro model to demonstrate the effects. For example, FIG. 7 illustrates one arrangement of a testing set-up 700 in which one or more cultured or explanted cells were examined optically (e.g., using a laser 703 coupled to a microscope imaging system 705) while applying low-voltage nanosecond pulses at high frequency through a pair of electrodes 707, 707' coupled to a system such as the one shown in FIG. 5. Using a system similar to that shown in FIG. 7, the use of megahertz burst compression was verified in several types of mammalian cells in vitro (e.g., CHO, HEK 293, and enzymatically isolated murine primary ventricular cardiomyocytes, VCM). The effect of electrical pulses in the nanosecond range was documented by time-lapse recording of cytosolic Ca2+ activation with a Fluo-4 fluorescent indicator and transillumination recording of cell shape changes. Depending on the cell type and other conditions and intensity of electrical pulses in the nanosecond range, these observations reflected cell membrane permeabilization, opening of voltage-gated calcium channels, contractile activity, and/or cell-reshaping, or other types of bio-effect due to membrane disruption.

Figure 8A:
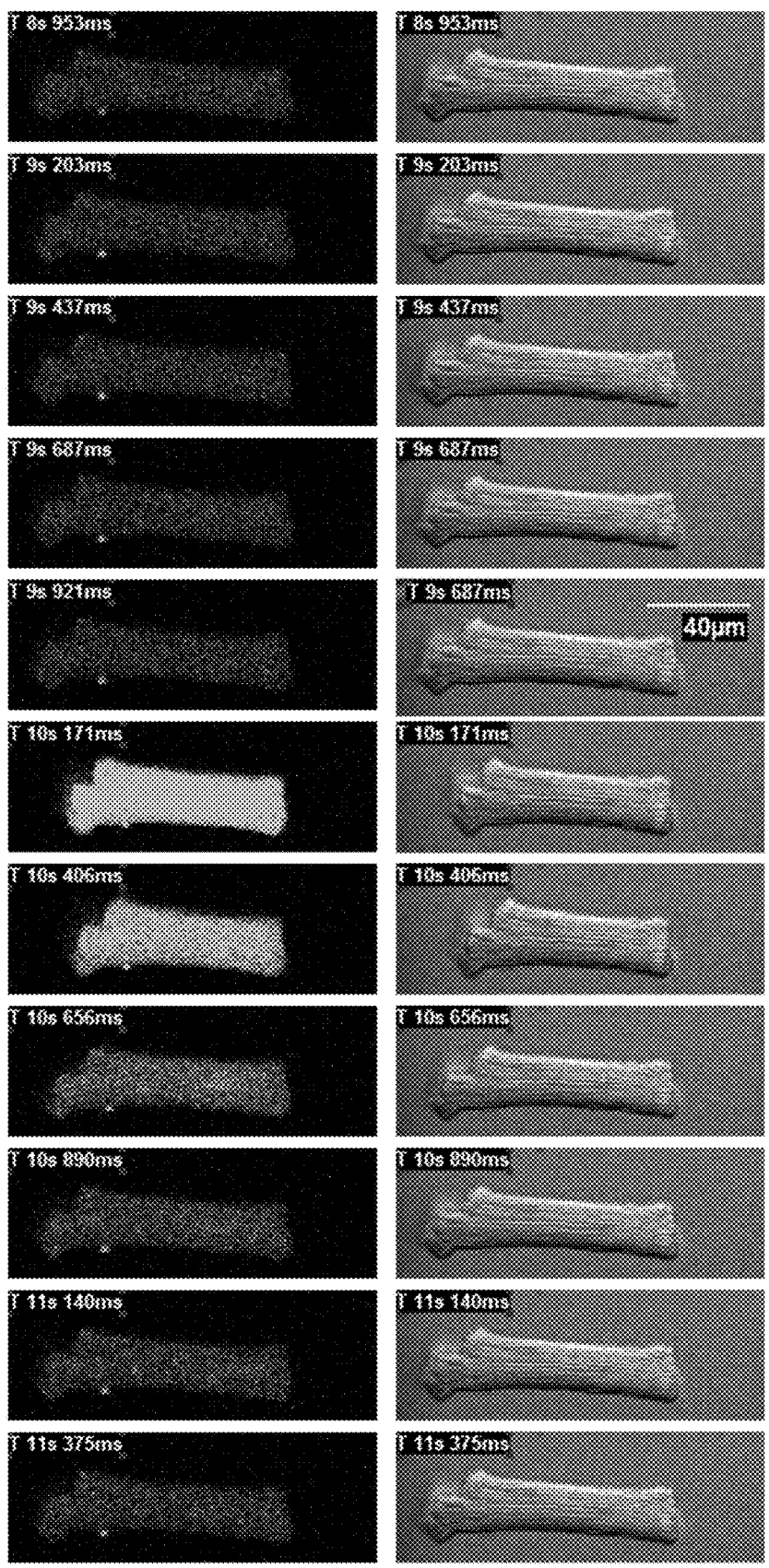
FIG. 8A illustrates an example of excitation of a mouse ventricular cardiomyocyte by nanosecond pulses at low electric field (e.g., 85 V/cm) and megahertz frequency (e.g., 3.33 MHz).

FIGS. 8A-8B, 9, 10, 11A and 12A-12B illustrate examples of testing of sub-microsecond (e.g., nanosecond) pulses, e.g., having pulse durations from 50 to 300 ns, focusing primarily on 200- and 300-ns stimuli. Pulses were delivered in bursts from 100 to 5,900 pulses, at repetition rates of between about 1.6 and 3.33 MHz, which corresponded to inter-pulse intervals from about 150 to 450 ns. The pulse amplitude was varied from between about 2 to 17 V, with the resulting electric field from about 70 to 570 V/cm, respectively, at the cell location. A total of about 200 pulses of electrical stimulation in the nanosecond range treatments in 26 individual VCM and more than 80 nanosecond pulses in treatments in other cell types (>120 individual cells) were examined. Cell responses were consistently recorded (as shown in FIGS. 8A-12B) despite extremely low pulse amplitudes (as compared to standard treatments using pulsed electric fields in the nanosecond range). The lowest electric field that caused VCM activation and contraction was only 85 V/cm (e.g., FIG. 8A, showing a burst of 1,000 pulses, 200 ns pulse duration, 3.33 MHz). This was a >30-fold reduction of the electric field compared to the published threshold of about 2.5 kV/cm for 200-ns pulses (including single 200 ns pulses). A slightly higher electric field, about 160 V/cm, caused calcium activation (excitation) and cell contraction in 17 out 18 VCM which were tested and proven functional and capable of generating this type of response. The threshold did not show significant dependence on whether cells were oriented parallel or perpendicular or at any other angle to the electric field. At this low electric field using nanosecond pulses in the megahertz frequency range, excitation in individual VCM could be repeated multiple times (see, e.g., FIG. 8B) with no signs of electroporation or damage. Increasing the electric field about 2-fold above the excitation threshold resulted in the observation of modest membrane disruption, such as spontaneous sparkletts and elevation of resting level of cytosolic Ca2+. Further increase in the electric field, to only about 400+/−18 V/cm caused irreversible VCM electroporation, with no recovery of cytosolic Ca2+ and transformation of VCM from a healthy "brick shape" to a "meatball shape", a recognized manifestation of permanent VCM damage. See, e.g., FIGS. 8B and 11A and the last trace in FIG. 9). In general, the excitation response was also observed with shorter pulse trains, such as 400 or 500 pulses, 3.33 MHz at 0.16 kV/cm, as well as with shorter 100-ns pulses (3900 pulses, 2 MHz, at 570 V/cm). VCM were repeatedly excited with trains of tens of compressed nanosecond electrical pulse bursts applied every 2 s (data not shown).

Figure 8B:
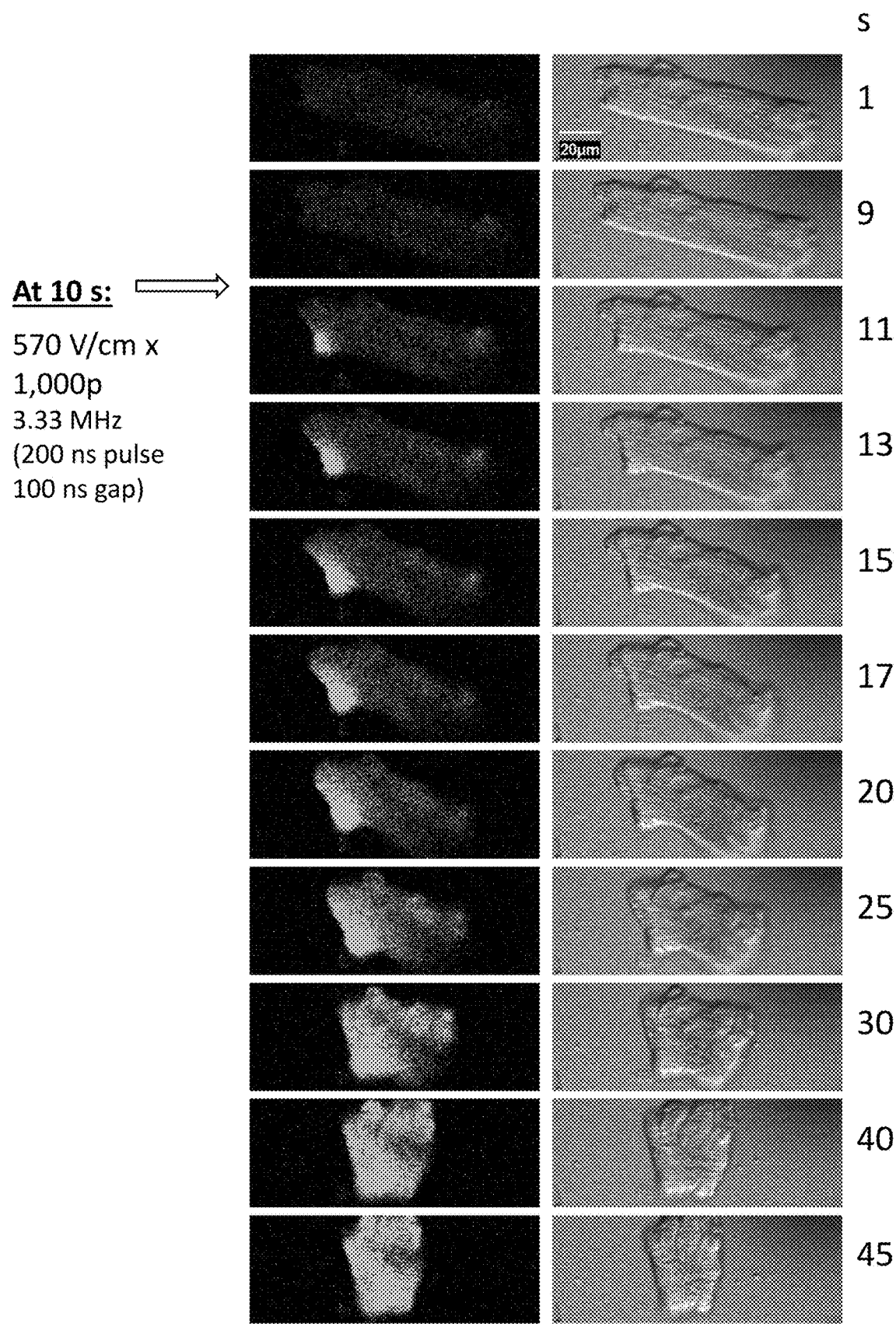
FIG. 8B illustrates an example of irreversible cell damage (e.g., poration of the cell, causing cell death) by applying nanosecond electrical pulses at low electric field (e.g., 150 V/cm) and megahertz frequency (e.g., 3.33 MHz).
Figure 9:
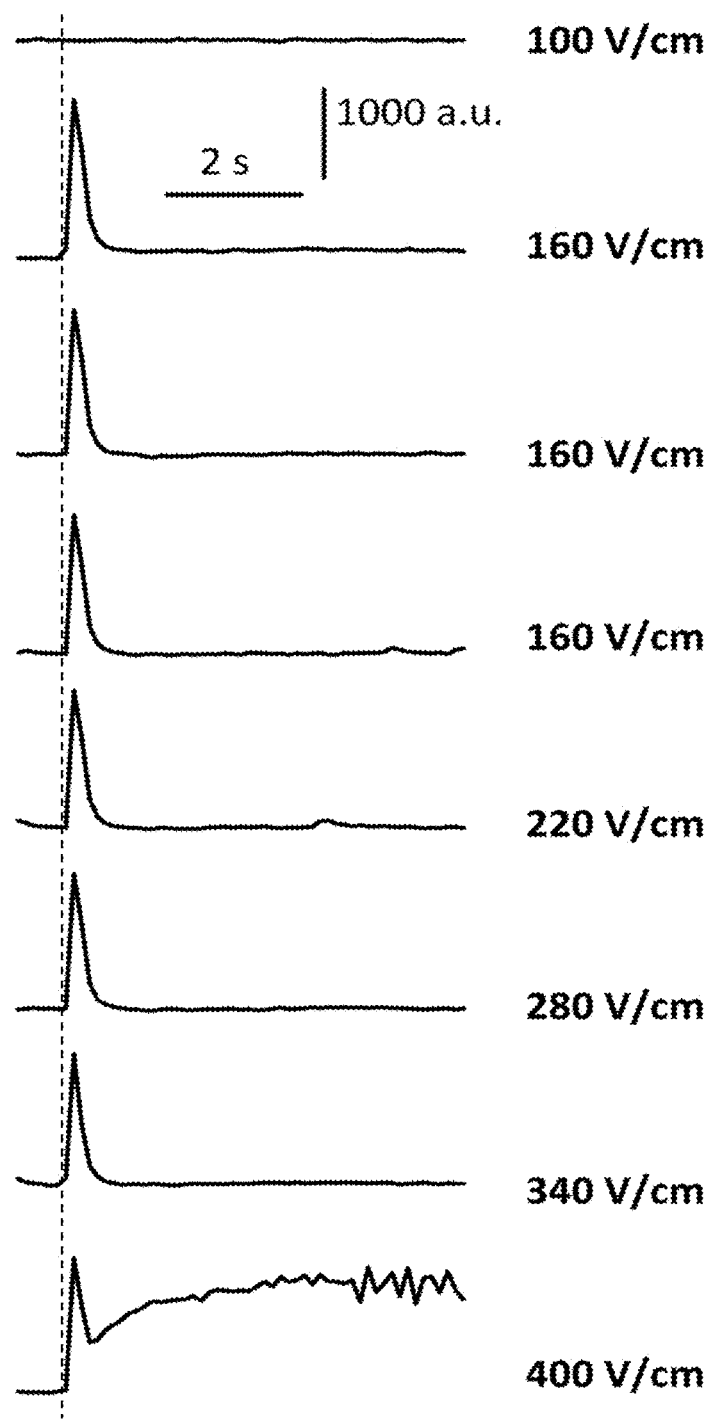
FIG. 9 illustrates the effect of repeated excitation of a ventricular cardiomyocyte by a bust of 1000 nanosecond pulses (e.g., 3.33 MHz, 200 ns width) at between 160-340 V/cm. Excitation was applied at the time indicated by the vertical line. Excitation resulted in a spike in cytosolic Calcium concentration, imaged using Fluo-4 dye. A first threshold for excitation was reached at 160 V/cm, resulting in the non-destructive influx of calcium. Above 400 V/cm cell destruction occurred. Same bursts at 100 V/cm caused no effect, whereas at 400 V/cm the excitation was followed by a prolonged Ca2+ increase (a sign of electroporative damage to cell membrane).
Figure 10:
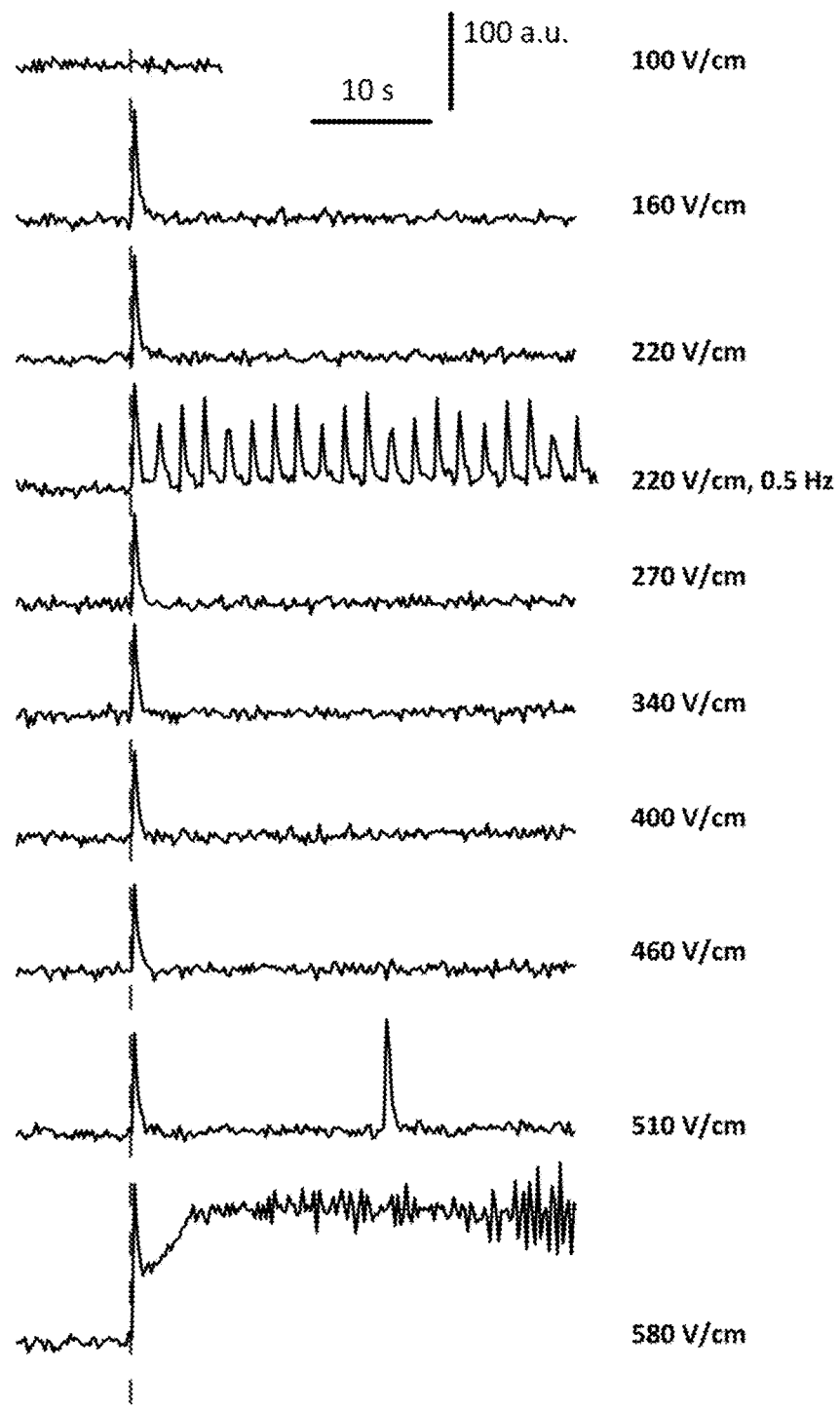
FIG. 10 is another example showing repeated excitation of ventricular cardiomyocytes similar to that shown in FIG. 9. Although the thresholds for excitation are slightly different, similar effect is seen.
Figure 11A:
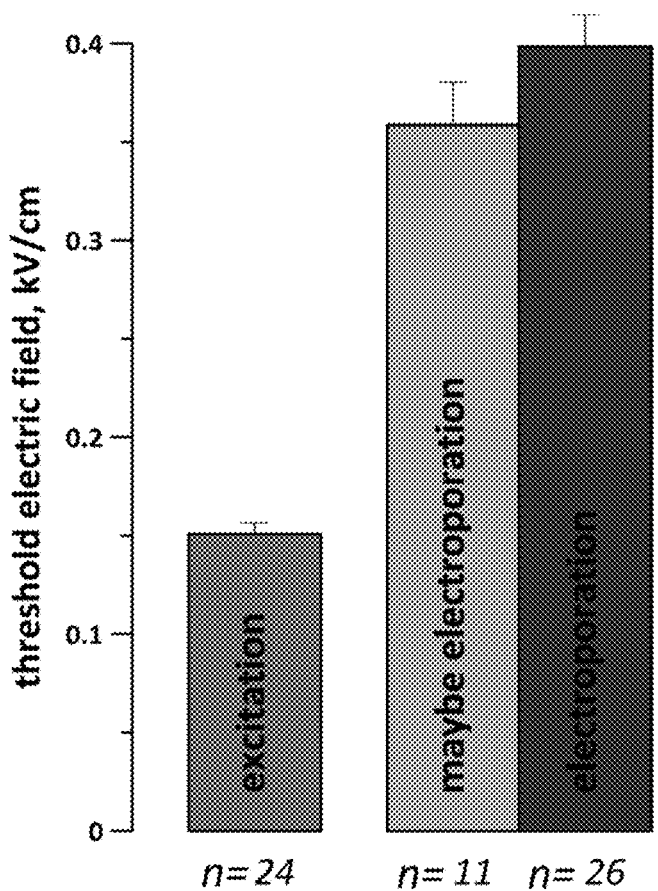
FIG. 11A is a bar graph showing the threshold electric field for excitation, possible electroporation and definite electroporation in murine ventricular cardiomyocytes exposed to a train (e.g., burst) of 1000 nanosecond pulses (at 3.33 MHz, 200 ns width pulses). Excitation was evidenced by a brief spike in cytosolic Ca2+ concentration as imaged with Fluo-4 dye. The appearance of a low-amplitude spontaneous Ca2+ fluctuations following stimulation was regarded as a possible sign of electroporative membrane disruption ("maybe electroporation"). Uncontrolled increase of Ca2+ without return to resting level within 40 s of observation (such as in bottom trace in FIG. 9) was considered evidence of electroporation.
Figure 11E:
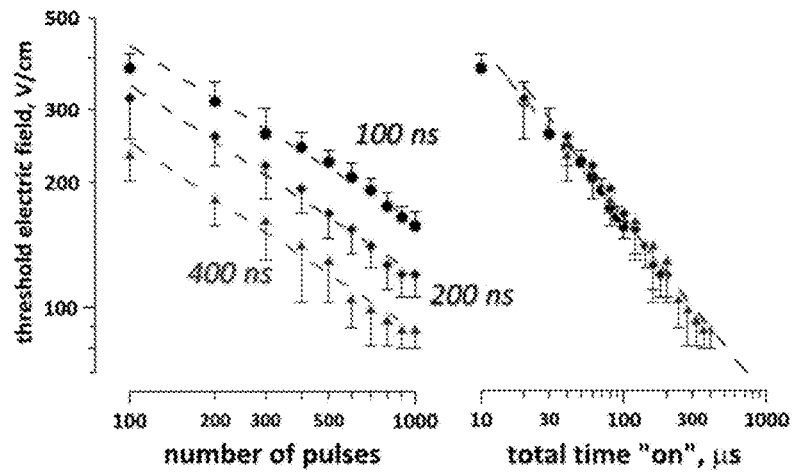
Figure 11E:
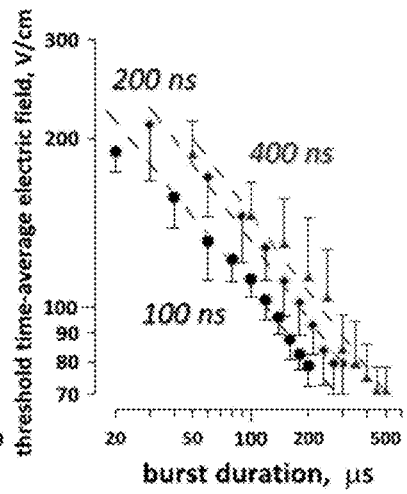
Figure 11E:
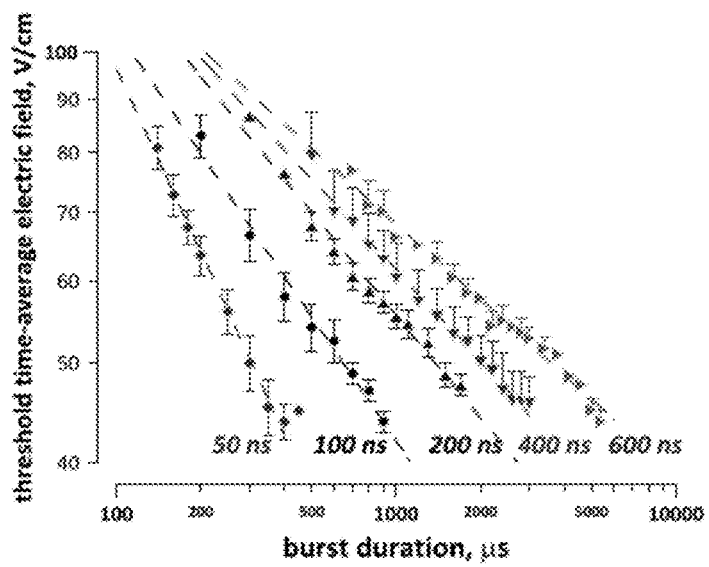

As shown in FIGS. 8A-8B, bursts of high frequency, sub-microsecond, low electric field electrical energy may be used for stimulation and/or electroporation of mouse ventricular cardiomyocytes (VCM). In some variations, high frequency, sub-microsecond, low electric field stimulation may be used for defibrillation. As described herein, the previously-limiting need for high voltage can be offset by applying high-rate bursts. For example, compressing 1000, 200-ns pulses into 3.33 MHz bursts enabled excitation at only 80-200 V/cm, as shown in FIGS. 8A, 9 and 11A, which is 10-20 times lower than with a single 200-ns shock. Excitation by such high frequency, sub-microsecond, low electric field stimulation bursts (as shown in FIGS. 8A and 9) was distinctly different from the persisting $Ca^{2+}$ elevation and cell shrinkage following membrane damage by stronger electric field (as shown in FIG. 8B). VCM excitation by a single low frequency (e.g., <1 MHz), sub-microsecond, high electric field (e.g., greater than 1 kV/cm) stimulation pulse was damaging at the excitation threshold, causing abnormal action potentials and long-lasting $Ca^{2+}$ elevation. This phenomena was generally true; in contrast to the lower-frequency, sub-microsecond, high electric field stimulation, the high frequency, sub-microsecond, low electric field stimulation described herein was substantially less damaging, while being highly effective.

For example, as shown in FIG. 9, repeated stimulation with MHz bursts caused no damage. Initial signs of electroporation were observed at 350-400 V/cm (see, e.g., FIGS. 8B and 11A), i.e., 2-3 times above the excitation threshold (p<0.001), allowing for a large safety window. With a fixed 100-ns interval between sub-microsecond pulsed stimulation, thresholds decreased as a power function for pulse widths from 100 to 400 ns (see, e.g., FIG. 11B). The threshold was determined by the total time "on" within bursts, whereas the individual high frequency, sub-microsecond, low electric field pulse duration did not matter (see, e.g., FIG. 11C). The threshold time-average electric field was plotted against burst duration was smaller for shorter pulses (FIG. 11D).

This unexpected result was verified in a separate set of experiments where VCM were excited by bursts of 1000 pulses; pulse duration was varied from 50 to 600 ns, and the interpulse intervals were changed from 90 ns to 4.8 μs. Plotting the time-average threshold electric field values against burst duration yielded significantly smaller values for shorter pulses (FIG. 11E), consistent with the previous experiment in VCM but contrasting nerve excitation (see, e.g., FIGS. 16A-16D, below). This may be indicative of a specific effect of sub-microsecond pulsing, distinctly different from conventional pulses.

Figure 12A:
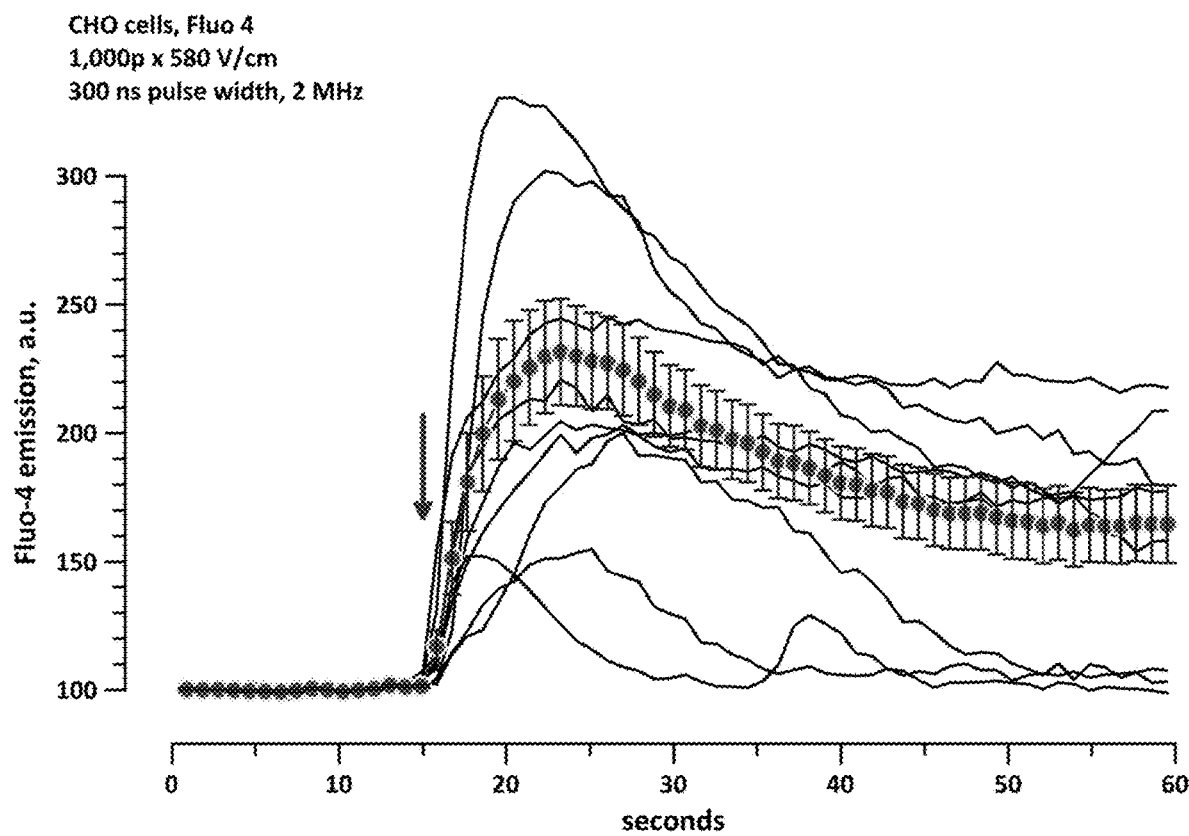
FIG. 12A is a graph summarizing the effect of applying a train of nanosecond pulses at 2 MHz to CHO cells (in this example, nanosecond pulses are 300 ns duration at 580 V/cm). A line, including error bars, showing mean values for all 8 cells examined is included.
Figure 12B:
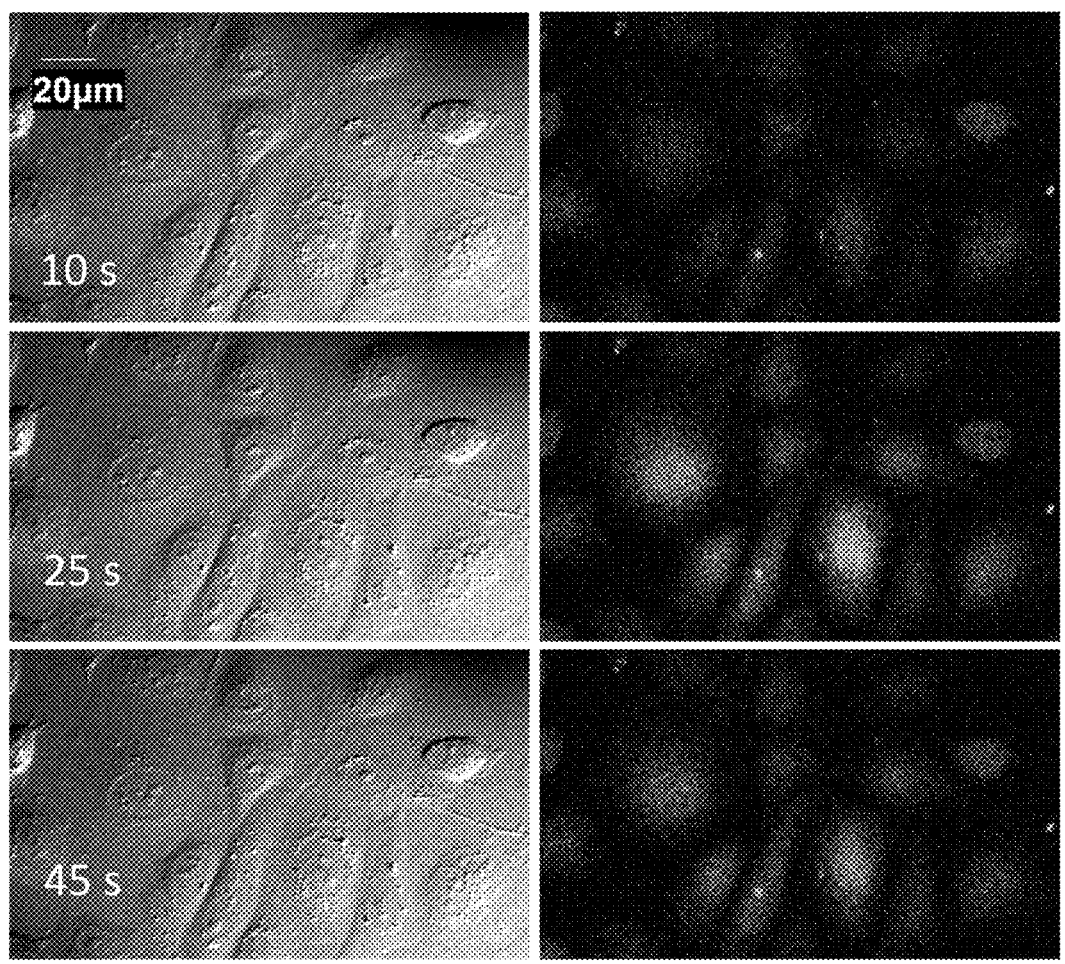
FIG. 12B illustrates electroporation of CHO cells (DIC images on the left, Fluo-4 emission on the right) over time following application of the nanosecond pulses based on the same data as shown in FIG. 12A. This figure shows representative DIC (left side) and Fluo-4 emission (right side) images of the same cells at the indicated time points.

In HEK293 and CHO cells, megahertz compression of bursts of pulses in the nanosecond range elicited Ca2+ transients, with either complete or partial recovery within 40-s observation after the stimulation, as shown in FIGS. 12A-12B. In contrast to VCM which were subjected to pulses in the nanosecond range as one cell at a time, these cultured cells were exposed as small groups. The probability and the amplitude of response increased for higher electric fields (range tested: 130-570 V/cm), higher pulse numbers (range tested: 100-1,000), and shorter interpulse intervals (range tested: 150-300 ns). The pulse duration was kept constant at 300 ns, to facilitate comparison with published work. Typical nanosecond pulsing at lower frequencies (including single pulsing) had a threshold of response to 300-ns pulse(s) at about 1.8 kV/cm. CHO cells do not express any voltage gated Ca2+ channels, and thus it is believed that Ca2+ transients are a result of electroporation.

Based on this experimental work, megahertz compression of nanosecond bursts (e.g., the application of low-voltage nanosecond pulses in the megahertz frequency range) enabled profound reduction of electrical energy thresholds for both excitation and electroporation. Surprisingly, there was also a clear separation of excitation and electroporation thresholds (see, e.g., FIG. 11A) and repeated excitation without damage, which has been problematic when using traditional electric pulsed fields in the nanosecond range.

The Application of Megahertz Compression of Nanosecond Bursts

As discussed briefly above, any of the methods and apparatuses (e.g., devices, systems, applicators, etc.) described herein may be used to treat tissue. Any appropriate tissue may be treated, including, but not limited to: skin, liver, kidney, neuronal (brain, spine, peripheral), lung, muscle, adipose, respiratory, gastrointestinal, bladder, reproductive, etc. tissue, including tumorous tissue. The nanosecond pulses at low electric field (e.g., low voltage) and high (e.g., megahertz) frequency described herein may be used to manipulate biological functions and treat diseases. Responses to such electrical stimulation may include a variety of bio-effects, including but not limited to: nerve and muscle excitation, activation of immune (or otherwise stimulating an immune response) and endocrine cells, cell differentiation, electroporation, necrotic and apoptotic cell death. Thus, the use of nanosecond pulses at low electric field and megahertz frequency may be used in virtually any indication in which electrical stimulation may be applied. In general, any of the high frequency nanosecond pulse generators and methods of using them described herein may be used for a medical therapy.

For example, the methods and apparatuses of the present disclosure may be used for cardiac pacing, defibrillation, muscle training and rehabilitation, pain control, alleviation of Parkinson disease symptoms, psychiatric disorders, and cancer ablation. They may also be used in neuromuscular and psychiatric disease diagnostics and research.

For example, devices, systems and methods described herein may be utilized in various ablation procedures (e.g., radiation-based), dermatological procedures (e.g., treating various dermatological conditions, such as skin cancers), general surgery procedures (e.g., pancreatectomy), cardiology (e.g., valve repair), gynecology (e.g., hysterectomy), neurosurgery (e.g., tumor resection) etc.

Any of the methods described herein may be applied to excitable tissues (including but not limited to neuronal tissues) for either excitation and/or ablation or other tissue treatments. For example, described herein are methods and apparatuses for the stimulation of excitable tissues such as nerve and heart muscle, the treatment of neurological disorders such as epilepsy, Parkinson's disease and stroke. Heart disorders could include atrial fibrillation and ventricle fibrillation. As demonstrated above, the membrane potential of one or a group of cells may be excited directly using the methods described herein. The methods and apparatuses described herein may be used to stimulate secretion in cells such as platelets.

The methods and apparatuses described herein may find particular use in treating the brain, peripheral nerves, muscles, and heart. As mentioned above, these methods may be used to for cardiac pacing, defibrillation, deep brain stimulation in Parkinson's disease, functional nanosecond electrical pulses for restoring functionality of skeletal muscles, and pain control to the emerging applications in fibromyalgia, depression, dementia, epilepsy, diabetic neuropathy, and many others. In particular, the nanosecond pulses at low electric field (e.g., low voltage) and high (e.g., megahertz) frequency described herein may be used to treat any indication in which it may be beneficial to modulate or introduce action potentials (AP) in nerve and muscle targets. For example, the methods and apparatuses described herein may be used for modulation (e.g., shifting) of resting potential, changing the synaptic efficiency. AP induction is accomplished by creating a transient voltage gradient at the target, either through the inserted or implanted electrodes, or non-invasively from the surface. Alternatively or additionally, any of the methods and apparatuses described herein may be used for electroporation.

Any of the tissues described herein may be selectively modulated using the application of megahertz compression of nanosecond pulses by applying trains of low-voltage nanosecond pulses in the megahertz frequency range. In some variations the methods described herein may modulate the cell based, at least in part, on the size of the cell and/or the membrane content of the cell. For example, these methods may affect cells having a high time constant for discharge (e.g., higher capacitance) compared to other cells, which may be a function of the composition and/or size of the cells.

For example, nanosecond electrical pulses at low electric field and megahertz frequency may be used to treat a patient's skin, including treatment of one or more of: acne, seborrheic keratosis, keloids, molluscum contagiosum, acrocordon, psoriasis, papilloma, human papilloma virus (HPV), melanoma, melasma, sebaceous hyperplasia, syringoma, congenital capillary malformation (port-wine stains), melasma, actinic keratosis, dermatosis papulosa nigra, angiofibroma, skin tumors, aging skin, wrinkled skin, cherry angioma, epidermal/sebaceous cyst, basal cell carcinoma, aging skin, benign tumors, precancerous tumors, cancers and warts. These methods and apparatuses may also be used for cosmetic skin treatments, including tattoo removal, hair follicle destruction, scar/keloids reduction, fat reduction, and wrinkle reduction. For example, the methods and apparatuses described herein may be useful for treating melanomas by causing them to self-destruct. In general, these methods may be useful for in vitro treatment of skin lesions.

The methods and apparatuses described herein for applying nanosecond electrical pulses at low electric field (e.g., low voltage) and high (e.g., megahertz) frequency may be useful for nanoelectroablation and vaccination.

Thus, the methods and devices described herein may be used in treatment of various diseases. A "disease" includes any abnormal condition in or on a subject that is associated with abnormal, uncontrolled growths of tissue, including those that are cancerous, precancerous, and benign, or other diseases as known in the art. The methods and devices of the present invention can be used for the treatment of any type of cancer, whether characterized as malignant, benign, soft tissue, or solid, and cancers of all stages and grades including pre- and post-metastatic cancers. Examples of different types of cancer include, but are not limited to, digestive and gastrointestinal cancers such as gastric cancer (e.g., stomach cancer), colorectal cancer, gastrointestinal stromal tumors, gastrointestinal carcinoid tumors, colon cancer, rectal cancer, anal cancer, bile duct cancer, small intestine cancer, and esophageal cancer; breast cancer; lung cancer; gallbladder cancer; liver cancer; pancreatic cancer; appendix cancer; prostate cancer, ovarian cancer; renal cancer (e.g., renal cell carcinoma); cancer of the central nervous system; skin cancer (e.g., melanoma); lymphomas; gliomas; choriocarcinomas; head and neck cancers; osteogenic sarcomas; and blood cancers.

These methods and apparatuses may also or alternatively be useful for ablating cancer and generating resistance to new cancer growth, including treatment of tumors. Examples of tumors include a benign prostatic hyperplasia (BPH), uterine fibroid, pancreatic carcinoma, liver carcinoma, kidney carcinoma, colon carcinoma, pre-basal cell carcinoma, and tissue associated with Barrett's esophagus.

The methods and apparatuses described herein may be used for gene-electrotransfer or "GET". In some variations the disease, including cancer, may be treated by transfer of genes (e.g., in one or more plasmids coding for genes that could stimulate an immune response) being introduced into tumors. For example, melanoma may be treated using a plasmid containing the gene for interleukin 12 (IL-12), which may stimulate the differentiation of naïve T cells into Th1 cells as well as the production of interferon-gamma and tumor necrosis factor-alpha. Alternatively, any of the methods and apparatuses described herein may be used to porate cells of a tissue, including in particular, tumor cells. This may permeabilize cells by generating pores large enough to allow the transport of small molecules across the plasma membrane. As shown in FIGS. 8A-8B, both reversible and irreversible electroporation may be achieved. For example, the methods and apparatuses described herein may be used for electrochemotherapy (ECT) may be used for the treatment of several cutaneous tumor targets, including melanoma, basal cell carcinoma, breast cancer and Kaposi's sarcoma (which may include the use of bleomycin, cisplatin, or other drugs). The methods and apparatuses described herein may be used to cause irreversible electroporation (IRE) which may lead to necrosis. For example, the methods and apparatuses described herein may be effective to treat, among other indications, prostate, brain tumor ablations (including gliomas), pancreatic cancer, colorectal liver metastases, unresectable renal tumors and rectal neoplasms.

The megahertz compression of nanosecond pulse trains described herein may be particularly effective in treating diseases including cancers because they may penetrate into the intracellular region of the cell(s). The ability to penetrate beyond the plasma membrane (possibly due to the pulse rise time reaching full amplitude in the nanosecond range) is typically much faster than the time required for intracellular and intraorganellar charges to redistribute to cancel the imposed field. This may allow the methods and apparatuses described herein to permeabilize small organelles by applying electrical pulses in the nanosecond range (e.g., including vesicles, mitochondria, endoplasmic reticulum and nuclei).

The methods and apparatuses described herein may also be useful for platelet activation (in the absence of thrombin); for example, these methods may be used for applying electrical pulses in the nanosecond range of platelet-rich plasma to improve wound healing and enhance blood flow.

As mentioned, above, the megahertz compression of nanosecond pulse bursts described herein may be used to influence tumor growth; for example, to treat tumors with electrical pulses in the nanosecond range at low electric field and high frequency, e.g., megahertz, so that the tumor disappears over days to weeks, and may exhibit characteristics of immunogenic cell death (ICD), e.g., releasing DAMPs such as calreticulin translocation from the ER to the cell surface, ATP release and HMGB1 release. These methods may also be used to inhibit metastasis.

Similar to the use of pulsed electric fields in the nanosecond range using high voltages (e.g., 30 kV/cm) the methods described herein may also provide treatments that are drug-free, very fast and leave no scar, and may be treated with only one or a few treatments. However, unlike other pulsed regimes, the methods and apparatuses described herein do not require a large electric field to achieve the desired effect (including immunogenic cell death effects). Thus, the size of the ablation zone may be larger and may be more easily applied and/or tolerated by the tissue.

It should be noted that the examples given herein are for the purposes of illustration and example only, the description as set forth is not intended to be exhaustive or limiting.

Megahertz Compression of Nanosecond Bursts with Bipolar Pulse Targeting

In general, the methods and apparatuses described herein for megahertz compression of nanosecond bursts, e.g., providing nanosecond pulses at low electric field and high (e.g., megahertz) frequency, may be used with multiple sources for applied electrical energy (e.g., electrodes, antenna, etc.). For example, two sets of electrodes may be used to apply energy from separate regions on, in, or around the tissue, and the regions in which applied energy sums (e.g., by superposition) to generate a pulse train of sub-microsecond pulses at a frequency that is in the megahertz range (e.g., greater than or equal to about 1 megahertz), likely resulting in accumulation of charge at the cell membrane(s), the resulting megahertz compression may result in triggering a bio-effect at a substantially lower threshold as compared to applied electric fields that are pulsed at lower rates, including single pulses. As described above, this may be views as an apparent lowering of the threshold for triggering the bio-effect, in reference to the amount of energy that is applied.

Figure 13:
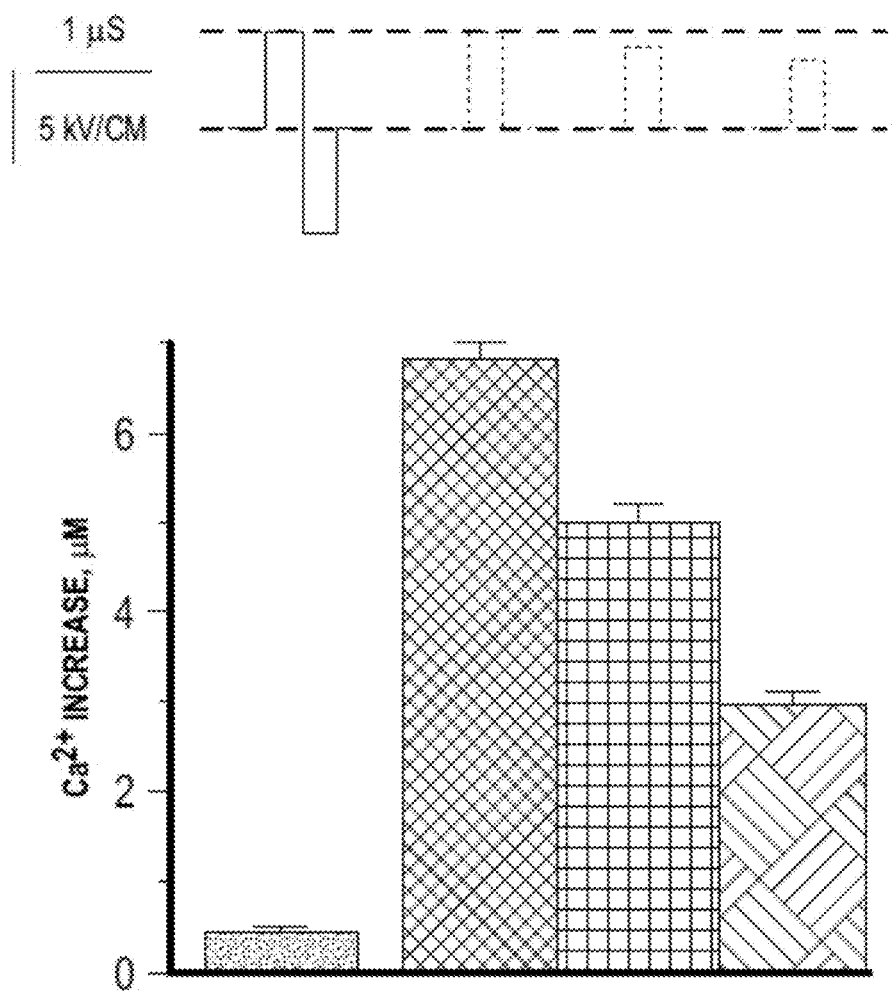
FIG. 13 illustrates bipolar cancellation.

In some embodiments of this application, the methods and apparatuses described herein for megahertz compression of nanosecond bursts, e.g., providing nanosecond pulses at low electric field and high (e.g., megahertz) frequency, may be applied in combination with the use of bipolar pulses in order to specifically target the treatment zone at a distance from the application of the electric pulses while minimizing the effect of the electrical pulsing at or near the electrodes (in non-target regions). U.S. application Ser. No. 16/104,089, filed Aug. 16, 2018 ("TARGETED REMOTE ELECTRO-STIMULATION BY INTERFERENCE OF BIPOLAR NANOSECOND PULSES") describes the use of bipolar, nanosecond pulses at high voltages from different but overlapping regions of a tissue to specifically target overlapping regions (referred to CANCAN). Interestingly, as shown in FIG. 13, nanosecond pulsed activation using bipolar nanosecond pulses at high voltage (e.g., high electric field strengths) does not result in activation of bio-effects in a cell membrane. As shown in FIG. 13, described in greater detail below, the use of bipolar nanosecond pulses appears to cancel out the effects of the nanosecond pulse on the tissue, likely because the bipolar nature of the pulse, in which the second half (e.g., a negative-going portion of the pulse) undoes any charge movement due to the first half (e.g., a positive-going) portion of the pulse. However, when two bipolar pulses overlap and are out of synch, which may happen when, for example, the pulses are applied from two different regions of the tissue and at different times, the electric field in the overlapping region may superimpose and result in a monopolar pulse in the overlapping region. Thus, the overlapping region may be affected by the resulting monopolar nanosecond pulsing even while the rest of the tissue is unaffected by the bipolar nanosecond pulsing.

The megahertz compression of nanosecond bursts may be combined with this CANCAN effect to provide highly effective electrical pulses (e.g., including but not limited to electrical stimulation) of even deep tissue regions. This megahertz compressed CANCAN technique may be particularly effective since the energy required to evoke an effect when using megahertz compression of nanosecond pulsing is dramatically lower than that required without megahertz compression. This effect may be even further enhanced by the use of antennas to emit the nanosecond bursts at high frequency (e.g., within the megahertz range).

Thus, also described herein are methods and apparatuses (see, e.g., FIG. 7), that emit multiple trains of bipolar nanosecond electrical pulses at high (e.g., megahertz) rates from different locations to form a region of overlap in which the multiple bipolar nanosecond pulsed trains superimpose to form a localized train of monopolar nanosecond pulses at low electrical filed. The resulting superimposed monopolar nanosecond pulses at low electrical filed may be above threshold for evoking a bio-effect (e.g., stimulation, poration, etc.) in the localized overlapping region.

The use of megahertz compression of nanosecond bursts with CANCAN may result in sharpening of the CANCAN effect. It is somewhat counterintuitive to combine the use of bipolar cancellation of CANCAN with megahertz compression of nanosecond bursts, since it is unlikely that megahertz compression would have any effect on bipolar pulsing from a single source (e.g., a single train of bipolar, nanosecond pulses at low electric field strength). Since there is an immediate discharge at every pulse (as in traditional bipolar nanosecond pulsing), a bipolar pulse train should not be amenable to megahertz compression, which may enhance the voltage effect at the membrane by temporally summing the charge between pulses. In addition, because the use of megahertz repetition rate allows substantially lower electric field strengths to be applied to achieve comparable bio-effects, these methods and apparatuses may compensate for attenuation due to tissue thickness. In addition, there may be much stronger (e.g., sharper) differences between bipolar and unipolar pulses, which may allow improvements in targeting. This may further allow enhanced biological effects (e.g., stimulation) from electrical pulses without electroporative damage, for example, in excitable tissue (e.g., neuronal tissue). For example, in some variations, two synchronized "CANCAN" pulse trains may be generated from four pairs of electrodes, which may overlap into longer pulses within the tissue depth.

Although the megahertz compression methods and apparatuses described herein may be used in conjunction with bipolar cancellation to reduce the effect of the pulsed electrical energy at the multiple sets of electrodes emitting the pulses, it should be understood that these methods and apparatuses do not need to use bipolar cancellation. As mentioned above, these methods and apparatuses may be used with any method or apparatus that applied pulsed sub-microsecond energy to create a biological effect, including methods and apparatuses that apply pulsed electric fields from multiple locations that may combine, by superposition within the tissue.

Thus, described herein are methods and apparatuses for performing nanosecond, bipolar, electrical pulses at high (e.g., megahertz) frequency from each of a plurality of different locations that are offset, in order to target a region of overlap at a distance from the plurality of different locations in which the overlap between the plurality of offset nanosecond, bipolar electrical pulses at high frequency results in a nanosecond, monopolar, electrical pulse train having a high (e.g. megahertz) frequency that is localized to the targeted region of overlap. For convenience, these methods and apparatuses for performing them may be referred to herein as megahertz compression of offset and overlapping bipolar nanosecond bursts.

For example, described herein are megahertz compression of offset and overlapping bipolar nanosecond bursts to specifically target the application of nanosecond electrical pulses at a distance from the application of the electrical pulses to selectively evoke a bio-effect in deep tissues and organs without inserting electrodes. The local superposition of bipolar stimuli of nanosecond duration (and at megahertz repetition rates) may increase the depth of penetration and precision of therapeutic and diagnostic treatments that utilize nanosecond electrical pulses. Exemplary applications of these methods and apparatus may include any of those mentioned above, including, but not limited to psychiatric disorders, Parkinson's disease, and pain control to targeted ablation of deep tumors, among many others.

Figure 14A:
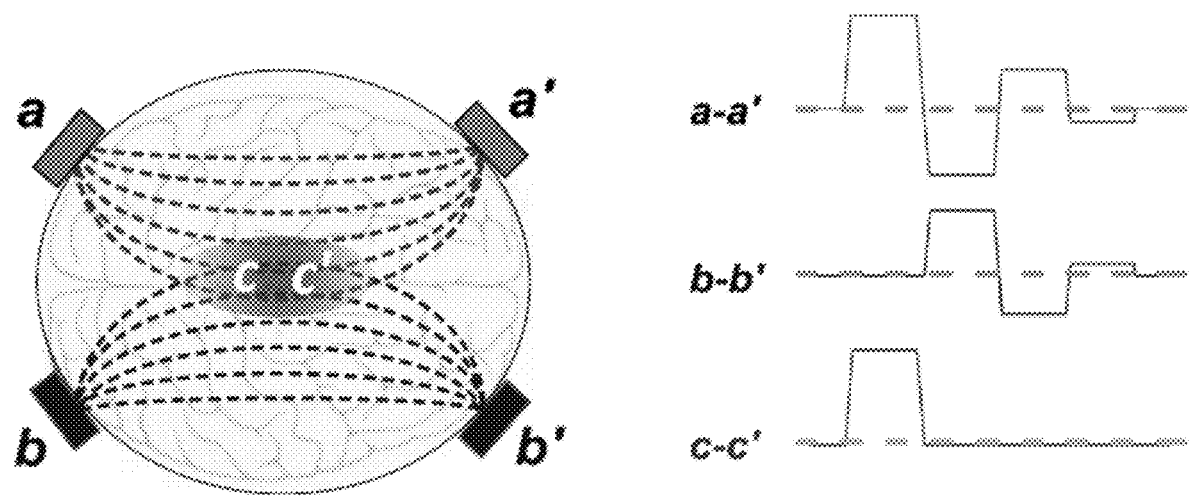
FIG. 14A illustrates megahertz compression of offset and overlapping bipolar nanosecond pulse trains (e.g., bursts), which may provide remote stimulation by superposition of two bipolar nanosecond pulse trains at high (e.g., megahertz) frequency into a unipolar electrical nanosecond pulse train at high (e.g., megahertz) frequency. The approach is illustrated for a rectangular train bipolar pulses and linear arrays of stimulating electrodes. Two pairs of independent, ground-isolated electrodes (a-a' and b-b') deliver two synchronized, nanosecond bipolar electric pulse trains as shown in the right side. Each of the nanosecond bipolar pulses is inherently inefficient for electrostimulation due to at least partial bipolar cancellation, but their superposition in the overlapping target region (c-c') forms a locally biologically-effective nanosecond unipolar pulse train at high frequency (e.g., in the megahertz rate) by adjusting the frequency of the pulse train between a-a' and b-b', as shown. The formation of a unipolar nanosecond pulse train in the c-c' area may be accomplished by controlling the timing and amplitudes of the energy applied between the electrodes a-a' and b-b'. Note that the bipolar cancellation is relevant at or near the electrodes, as it may reduce the effect of the pulsed electric field near the electrodes; in the remote target region, the monopolar field may benefit from the reduced thresholds resulting from the charge build up when using very rapid (e.g., megahertz) pulsing in the overlapping target region.

The megahertz compression of offset and overlapping bipolar nanosecond bursts may enable selective, non-invasive, localized electrical stimulation of deep targets. In certain embodiments, the disclosure relates to the use of the unique property of nanosecond electrical pulses to cancel their stimulatory effect following the reversal of the stimulus polarity as well as the high-frequency (megahertz) stimulation that may lower the threshold for evoking a desired biological response. In some embodiments, the second phase of a bipolar nanosecond electrical pulse cancels the stimulatory effect of the first phase, hence the entire bipolar stimulus becomes weaker than a half of it, as illustrated in FIG. 13. In turn, superposing two bipolar stimuli into a monopolar stimulus cancels the cancellation ("CANCAN") and restores the stimulus efficiency. An example in FIG. 14A shows how two bipolar pulse trains can produce a monopolar stimulus in the area c-c' away from the electrodes. The bipolar pulses may be repeated in the megahertz frequency. This technique may enable selective electrical stimulation at a location remote from electrodes, even where the resulting electric field is low (e.g., less than 1 kV/cm).

The methods and apparatuses for megahertz compression of offset and overlapping bipolar nanosecond bursts may be minimally disruptive (e.g., non-invasive). The methods and apparatuses disclosed herein also typically involve fewer procedural steps, lower cost, and fewer cells than pre-existing approaches. In addition, the methods and related aspects disclosed herein may also involve the use of consistent and precisely defined electric fields, efficient media exchange and application/removal of drugs, and addition to aseptic conditions.

Figure 14B:
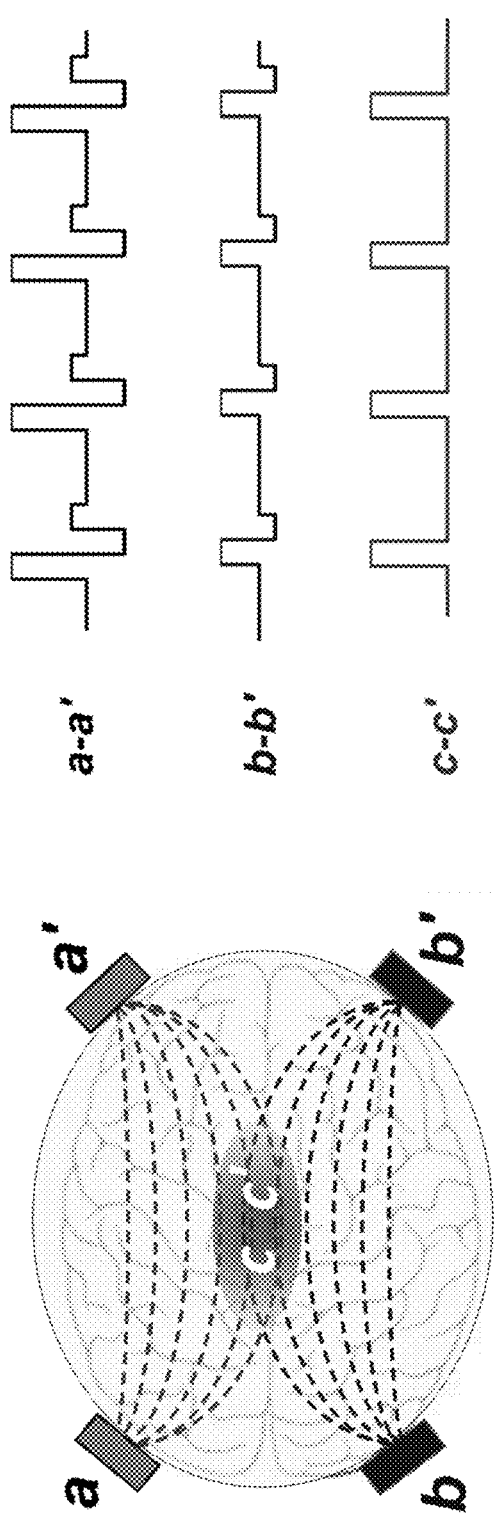
FIG. 14B is similar to FIG. 14A, but illustrates the use of pulse trains (e.g., sub-microsecond pulse trains) that combine in the target region c-c'.

In FIG. 14A, the first nanosecond pulse train between elements a-a' and the second nanosecond pulse train between elements b-b' may be configured as harmonics of each other, so that summation of the two pulse trains in region c-c' results in a sufficiently high frequency so that the threshold for the electric field to trigger a biological effect (e.g., depolarization, poration, etc.) is met by the summed pulse train. FIG. 14B illustrates a similar effect, showing the use of pulse trains that combine to form a monopolar pulse train of greater than about 1 megahertz frequency in the target c-c' region of the tissue; the electric field may be relatively low (e.g., <1 kV/cm) but may still trigger a bio-effect as described herein.

Figure 15A:
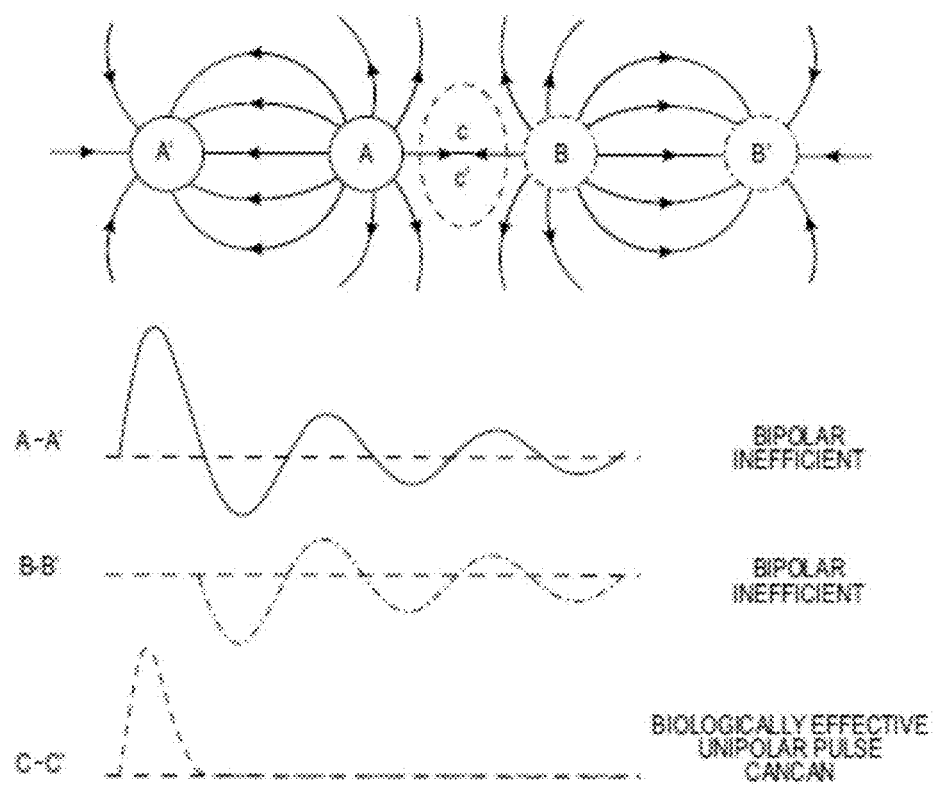
FIG. 15A shows a schematic illustrating the CANCAN concept according to one embodiment. Top: A-A' and B-B' are two independent pairs of electrodes. The lines between A and B represent the area to which the E-field is delivered from each pair of electrodes, which overlap and nullify each other in the region C-C'. Bottom: Each pair of electrodes delivers a damped sine wave (DSW), which are per se biologically inefficient. When the DSW from B-B' is phase-shifted, the two DSW superpose into a biologically-effective unipolar pulse in the C-C' area. In this region, there is "cancellation of cancellation," or CANCAN.
Figure 15B:
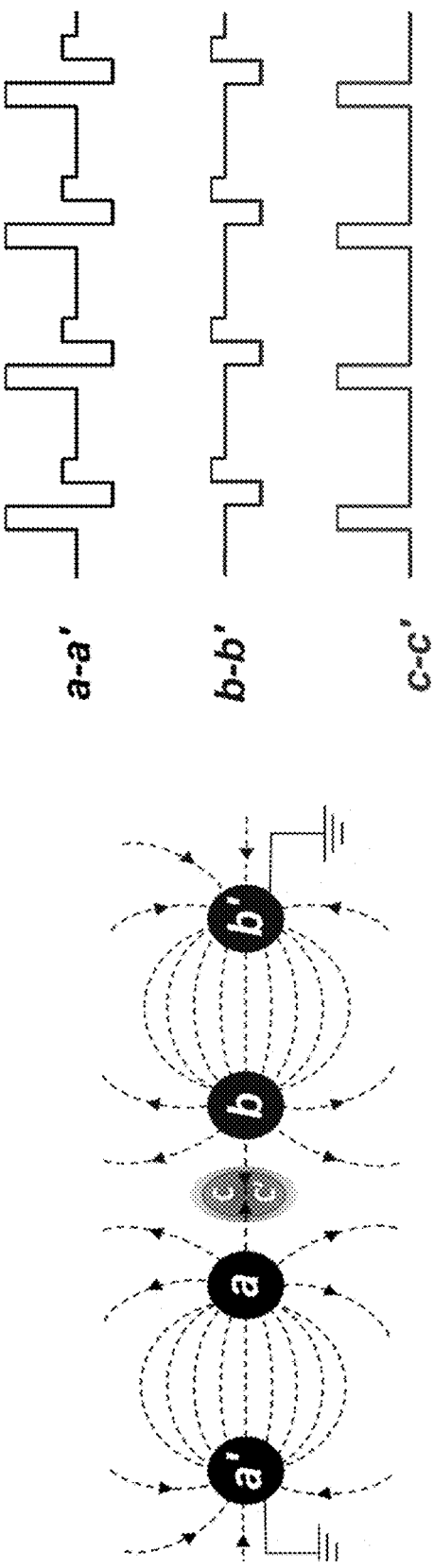
FIG. 15B is similar to FIG. 15A but illustrates the use of pulse trains (e.g., sub-microsecond pulse trains) that combine in the target region c-c'.

The methods and apparatuses for megahertz compression of offset and overlapping bipolar nanosecond bursts described herein may overcome the inherent inefficiency of bipolar nanosecond electrical pulses for targeted, non-invasive electroporation or electrostimulation. The megahertz compression of offset and overlapping bipolar nanosecond bursts described herein takes advantage of the fact that a bipolar electrical pulse on its own has a low biological efficiency. As illustrated in FIG. 15A, a damped wave (e.g., shown as a damped sinusoidal wave, DSW) applied between one pair of electrodes (A-A') is biologically ineffective. A second DSW that is phase-shifted (applied between electrodes B-B') is similarly ineffective. However, the superpositioning and synchronization of the two DSW creates a biologically effective unipolar pulse in a region distant from the two pairs of electrodes (C-C'). In other words, the effect of superpositioning the two biologically-ineffective DSW cancels the cancellation effect of the bipolar nanosecond electrical pulse, creating a unipolar pulse. This concept is referred to as a "cancellation of cancellation", or CANCAN, effect. FIG. 15B is a similar example, showing the use of pulse trains that combine to form a monopolar pulse train of equal or greater than about 0.1 megahertz frequency (e.g., 0.2 MHz or greater, 0.5 MHz or greater, 1 MHz or greater, etc.) in the target c-c' region; the electric field may be relatively low (e.g., <1 kV/cm) but may still trigger a bio-effect as described herein.

The superpositioning and synchronization of two properly shaped bipolar nanosecond electrical pulse trains, which are per se inefficient, restores a biologically effective unipolar pulse train remotely. This is because, at a certain location distant from the electrodes, the E-field produced during each subsequent phase which coincide in time nullify one another, so that what remains is only the first phase as a unipolar pulse. This nullification occurs when the E-field components from the two independent nanosecond pulse trains are opposite in direction, producing an |E| intensity of 0 kV/cm in that region.

One of the main goals for successful CANCAN is to have a lower effect compared to a unipolar pulse near the nanosecond electrical pulse-delivering electrodes, while creating an effect equal to that of unipolar remotely. E-field modeling results predict that a second phase amplitude of 70% may offer less E-field nullification near the electrodes more than a 50% second phase amplitude. This, in turn, may result in better bipolar cancellation near the electrodes when the two nanosecond electrical pulse trains are delivered synchronously. Therefore, in some variations the amplitude of only the second phase of a first pulse train may be 70% of phase A, while the amplitude of the third phase remained at 25%. With a second phase amplitude of 70%, there is less E-field nullification near the electrodes, causing the bipolar cancellation effect to predominate. In contrast, in the center between the electrodes, the effect is maximally different from asynchronous delivery, indicating maximal E-field nullification and CANCAN.

Remote electroporation by the superpositioning of two biologically ineffective bipolar nanosecond pulse trains into a biologically effective unipolar pulse train. This effect, termed cancellation of cancellation, or CANCAN, occurs when the E-field produced during the coincident phases of each bipolar nanosecond pulse is opposite in direction and nullifies each other, leaving only a unipolar exposure in a region distant from the electrodes, while remaining bipolar elsewhere. Consequently, CANCAN relies on the inherent inefficiency of bipolar nanosecond electrical pulsing for targeted electroporation. The efficiency of CANCAN is expected to be directly proportional to the extent of bipolar cancellation achieved.

The formation of a unipolar pulse remotely by megahertz compression of offset and overlapping bipolar nanosecond bursts presents the potential to access deep targets non-invasively. Megahertz compression of offset and overlapping bipolar nanosecond bursts may likewise extend to electrostimulation.

A similar effect, taking advantage of megahertz compression as descried above, and spatial summation, may be applied even without bipolar pulsing. For example, in some variations multiple low-electric field monopolar pulse trains that are below the gigahertz frequency may be emitted that, by themselves, have little, if any biological effect, however, when summed spatially in a target region, may result in a high-frequency (e.g., in the megahertz range), pulse train that is sufficient to result in megahertz compression of nanosecond bursts, triggering a bio-effect in the region seeing the summation.

EXAMPLES

As described above, tissue or cells (e.g., in some cases isolated tissue or cells, e.g., removed from the body), were used to confirm that the methods and apparatuses described herein may be use to effectively treat the cell and tissue. It should be understood that examples of isolated tissues and cells are for illustration only, and these techniques, methods and apparatuses (e.g., devices, systems, etc.) described herein may be used with intact or semi-intact tissues (e.g., organs, etc.) in a living human or animal as well.

For example, as described above in reference to FIGS. 7-13, cells were used to illustrate the methods and apparatuses described herein. For example, cells including adherent cell lines: HEK 293 (human epithelial kidney), CHO-K1 (Chinese hamster ovary) and mouse ventricular cardiomyocytes (VCM), were used for time-lapse fluorescence imaging assays, and suspension based EL-4 cells (e.g., mouse lymphoma) were used for viability studies. VCM were isolated from adult DBA/2 J mice by enzymatic digestion during Langendorff perfusion. VCM were seeded on laminin-coated 10-mm glass cover slips and used in experiments within 48 h.

The methods and apparatuses described herein may be used for stimulating electrically excitable cells. For example, nerve compound action potentials (CAPs) were evoked from nerves (n. ischiadicu+n. peroneus) from the bullfrog Rana catesbiana and CAP recording was performed. Isolated nerves were ligated at both ends and submerged in a chilled physiological solution containing (mM): 140 NaCl, 5.4 KCl, 1.5 $MgCl_2$, 2 $CaCl_2$, 10 glucose, and 10 HEPES (pH 7.3, 290-300 mOsm/kg, 1.6 S/m). CAPs were elicited with different generators described below and recorded with an MP160 Data Acquisition System (BIOPAC Systems, Goleta, Calif.).

In some experiments, bursts of 5 to 1000 pulses at repetition rates from 1 Hz to 3-4 MHz were used, with individual sub-microsecond pulsing duration ranging from 11 to 500 ns. Single pulses of up to 1 ms in duration were used to compare bioeffects with sub-microsecond bursts at various timing and intensity parameters. To deliver such diverse stimuli into different biological loads (impedance from 8 to 200 ohm), several high-power sub-microsecond generators as described herein were used, and in some cases a low-power model 577 digital delay generator (Berkley Nucleonics, San Rafael, Calif.) was used for comparison (although flexible for setting pulse parameters, the output of the model 577 pulse amplitude was limited to only 20 V into a 200-ohm load). The pulse generators configured as described herein may limit the burst duration and minimum pulse duration, but could deliver up to about 3 kV in 100-200 ohm loads (such as adherent cells on a coverslip), or up to 500 V into 8-10 ohm loads (such as an electroporation cuvette with cell growth medium). Except for cuvette exposure, pulses in these experiments were typically unipolar and nearly rectangular, with rise and fall times <15% of pulse duration (see, e.g., FIG. 16A). For cuvette exposure, long rise and fall times at the employed setting of 200 ns duration (at 50% height) resulted in a triangular pulse shape. In some examples, generation of single, nearly rectangular, unipolar long pulses (e.g., pulse duration of hundreds of microseconds) utilized either the model S88 stimulator or a custom-built MOSFET-based generator. In some examples, pulse shapes and amplitudes were controlled with a TDS3052 oscilloscope (Tektronix, Beaverton, Oreg.).

In examples showing cell stimulation and permeabilization, cell response to sub-nanosecond pulsing was monitored by time-lapse fluorescence imaging, to detect either changes of the membrane potential (e.g., with a FluoVolt dye), or increases in cytosolic $Ca^{2+}$ (e.g., with Fluo-4 or Fluo-8 dye, or YO-PRO-1 dye uptake). The membrane potential and $Ca^{2+}$ indicators were pre-loaded into cells, whereas YO-PRO-1 was added to the bath solution at 1 μM throughout the experiment. In some examples, the bath solution was either the physiological solution defined above, or (when indicated) the same solution mixed 1:9 with an isosmotic sucrose solution, to decrease conductance and facilitate electroporation. A pair of tungsten rod electrodes (100-um diameter, 140-170 urn gap) connected to a pulse generator were positioned within the microscope field of vision so that the selected cell (or a small group of cells) was centered between their tips; then the electrodes were lifted precisely to 50 μm above the coverslip surface. The pulsed power system was triggered and synchronized with image acquisition, e.g., by a TLL pulse protocol using a Digidata 1440A board and Clampex software (Molecular Devices, Foster City, Calif.). Electric field was calculated by 3D numerical simulations using a finite element solver COMSOL Multiphysics (Stockholm, Sweden).

In some examples, cell viability assays were performed. EL-4 cells where re-suspended in growth medium (DMEM with 10% FBS) at 1.2 10$^6$/ml, and 100-µl aliquots where placed in 1-mm gap electroporation cuvettes. Burst of sub-microsecond pulses were applied at room temperature; maximum (adiabatic) heating from the exposure was calculated as described elsewhere and did not exceed 6 degrees C. Cells were returned to the incubator, and viability was measured in 24 h with Presto Blue metabolic assay (ThermoFisher Scientific, Waltham, Mass.)

Peripheral Nerve Stimulation

Figure 16A:
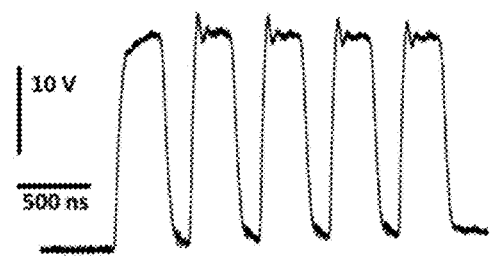
FIG. 16A shows an example of an applied pulsed electrical energy, at 60% duty cycle.
Figure 16B:
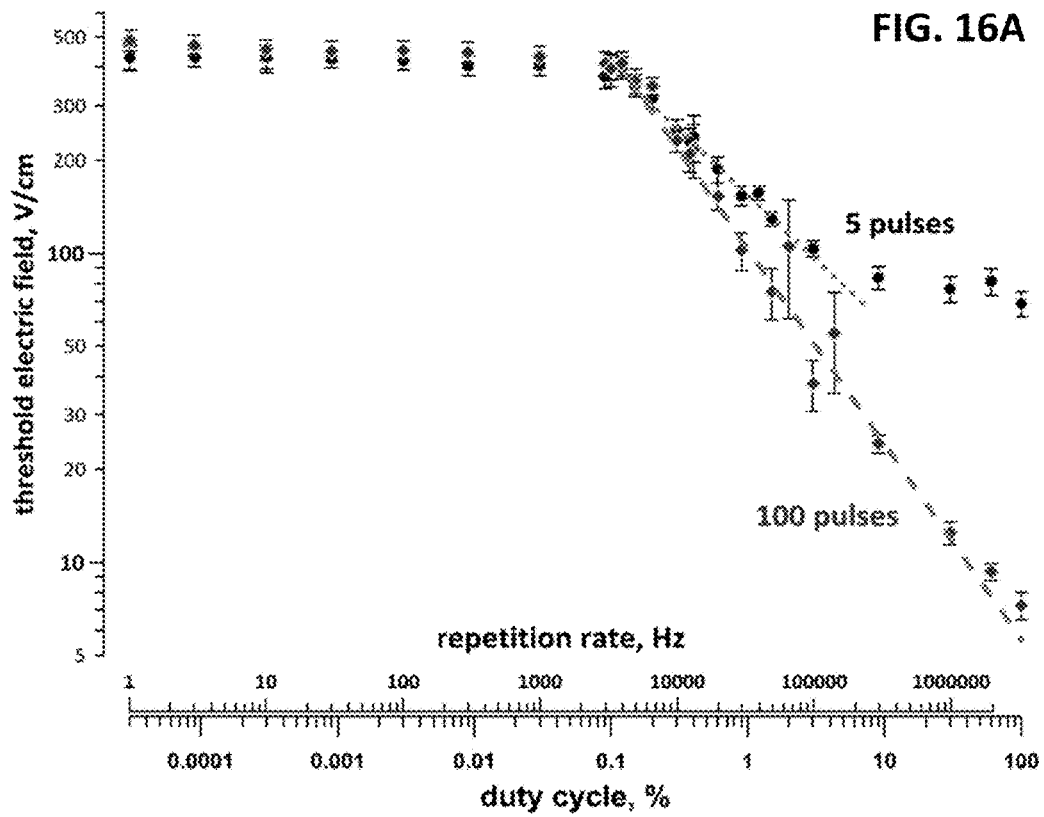
FIG. 16B is a graph showing the effect of pulse repetition rate on the threshold of excitation by bursts of 340-ns pulses, 5 or 100 pulses/burst.
Figure 16C:
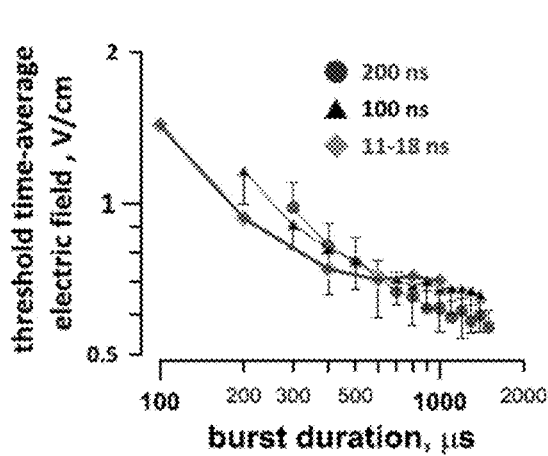
FIG. 16C is a graph illustrating the threshold time-average electric field decreases with burst duration, independently of indicated sub-microsecond pulse duration (11-18 ns is the duration range for the shortest setting in this example).
Figure 16D:
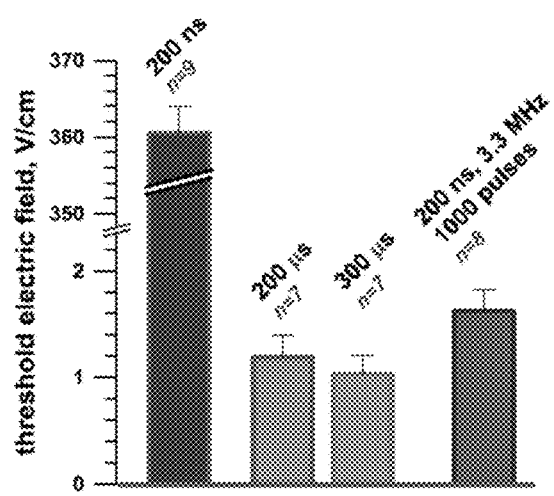
FIG. 16D is bar chart showing a comparison of excitation thresholds for single pulses of indicated duration and high frequency, sub-microsecond, low electric field bursts.

The methods an apparatuses described herein may be used to stimulate excitable cells. For example, peripheral nerves were stimulated using the methods and apparatuses described above. Nerve fibers can be repeatedly excited by high frequency (e.g., megahertz), sub-microsecond, low electric field (e.g., less than 1 kV/cm) stimulation without damaging the nerve. For example, as shown in FIG. 16B-16D, nerves were excited using sub-microsecond stimulation (similar to that shown in FIG. 16A). In FIG. 16B, 340-ns pulses were applied in 5- and 100-pulse bursts with repetition rates from 1 Hz to 2 MHz. In this example, there was no summation at rates up to about 7 kHz, so thresholds for the bursts likely equaled the threshold for a single 340-ns pulse. Summation at rates above 10 kHz is seen by the threshold reduction which followed a power function and was faster for 100-pulse bursts, which allow for a transmembrane potential build-up from a larger number of smaller pulses. At about 2 MHz, the threshold for 100-pulse bursts dropped from 400-500 to 10 V/cm for these cells. The threshold for 5-pulse bursts drops to a theoretical minimum (⅕ of the threshold for a single pulse) already at 0.3 MHz, suggesting a lack of any appreciable discharge between pulses.

The membrane potential induced by a sub-microsecond burst may be determined by the time-average electric field during the burst. This value can be calculated as the threshold electric field times the duty cycle. The threshold value of the time-average electrical plotted against the burst duration was found to be approximately the same regardless of the sub-microsecond pulse duration, as shown in FIG. 16C. Thus, the threshold for a single "long" pulse whose duration is equal to the burst duration may be predicted. As illustrated in FIG. 16D, a burst of 1000, 200-ns pulses at 3.3 MHz (duty cycle 67%, burst duration 300 µs) decreased nerve excitation threshold from 360±4 V/cm (for a single 200-ns pulse) to 1.63±0.2 V/cm. The time-average electric field during such a burst was approximately 1.63×0.67=1.1 V/cm. This was the measured threshold for a single 300-µs pulse (1.04±0.2 V/cm). Measured threshold for one 200-µs pulse (pulse duration equals total time "on" in the burst) was only marginally higher, e.g., 1.21+/−0.17 V/cm. However, a simple relation between the efficiency of high frequency, sub-microsecond, low electric field bursts and a single long pulse is not always valid. In general, the electric field required to produce the effect (e.g., in FIGS. 16B-16D, to excite the electrically excitable cell membrane) typically decreases as the repetition rate within the pulse burst increases (e.g., decreasing the delay between adjacent pulses). Although the precise values of the pulsing parameters (e.g., frequency, repetition rate/interpulse interval, etc.) may vary for different tissue types or cell types, the same general trends may apply.

Figure 17A:
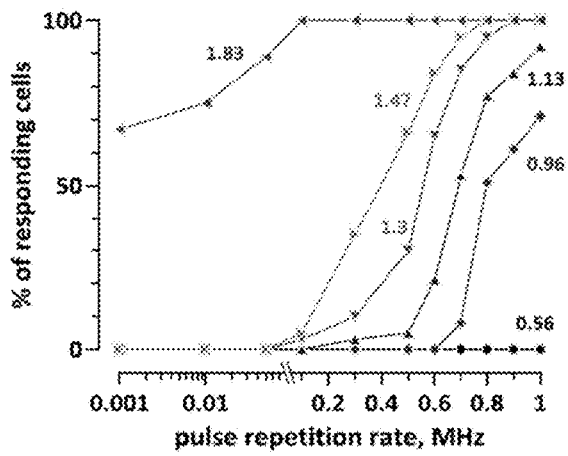
FIGS. 17A-17F illustrate one example of electroporation of CHO and HEK cells by high frequency, sub-microsecond, low electric field bursts evidenced by $Ca^{2+}$ uptake or YO-PRO-1 dye uptake.

As described above, the methods and apparatuses for high frequency (e.g., megahertz), sub-microsecond, low electric field (e.g., less than 1 kV/cm) pulsed stimulation may be used for electroporation of excitable and non-excitable cells. For example, FIGS. 17A-17F illustrates the electroporation of non-excitable cells by high frequency, sub-microsecond, low electric field pulse bursts. In FIGS. 17A-17F, electropermeabilization was measured in CHO and HEK cells, which do not express any voltage-gated channels. In FIG. 17A, a burst of 100, 400 ns pulses was delivered to CHO cells loaded with a Ca$^{2+}$ indicator Fluo-4. For different electric field strengths, pulse repetition rates were tested from 1 kHz to 1 MHz, and the number of cells which did and did not respond with a detectable Ca$^{2+}$ rise were counted. Each data point in FIG. 17A represents the responding fraction from a total of 20-30 cells from 3 or more independent experiments. The electric field values between about 0.96 and 1.47 kV/cm caused no Ca$^{2+}$ response at low repetition rates, but became increasingly more efficient at about 0.3 MHz and above. This frequency was about two orders of magnitude higher than for nerve stimulation (e.g., compare to FIG. 16B) and was consistent with the estimated charging time constant of about 1 µs. A higher electric field of about 1.83 kV/cm was efficient in 70% of cells at 1 kHz; the increase of the responding fraction at just 10 and 100 kHz is not fully understood, and may be a result of better detection since Ca$^{2+}$ transients also became stronger.

Figure 17B:
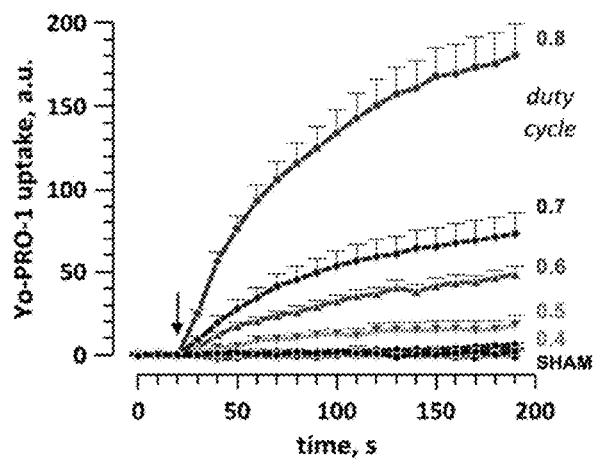
Figure 17C:
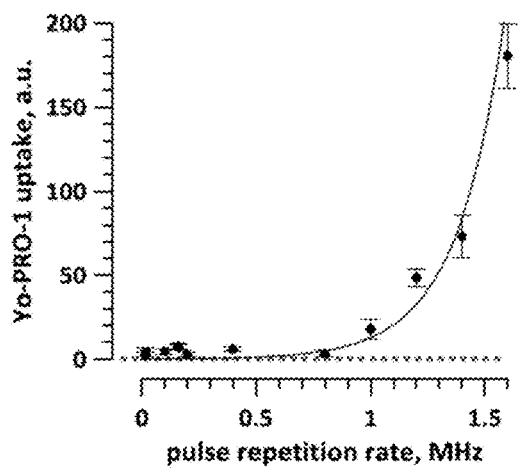
Figure 17D:
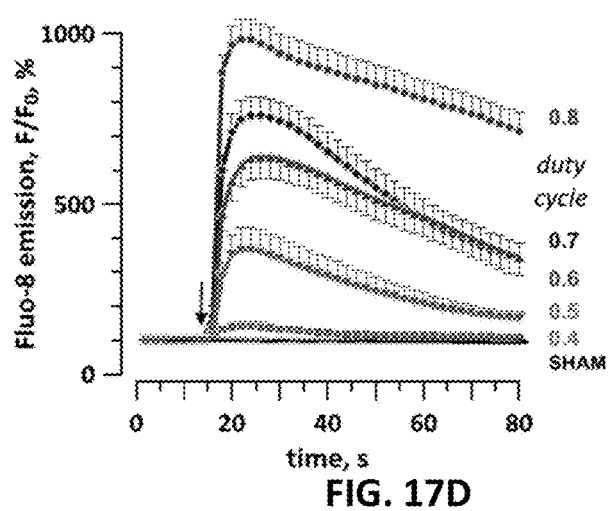
Figure 17E:
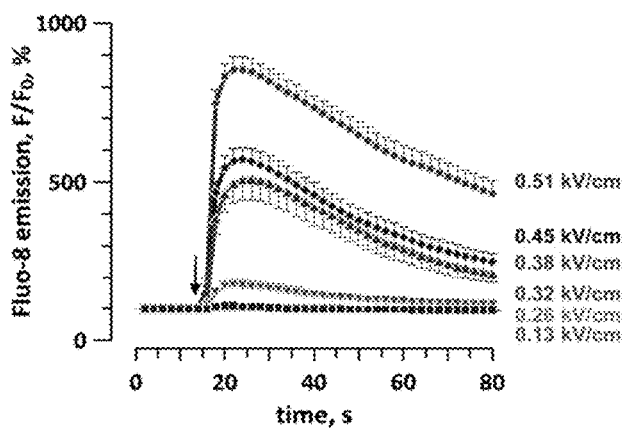
Figure 17F:
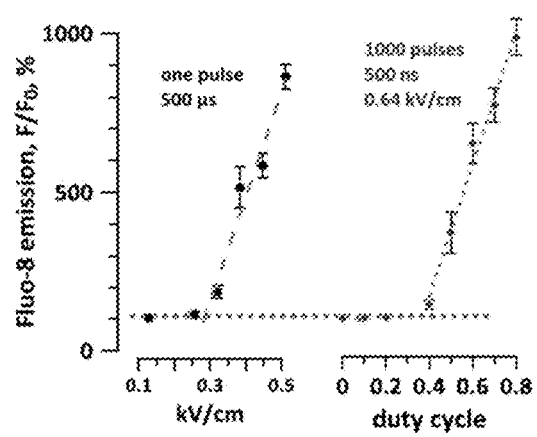
Figure 18A:
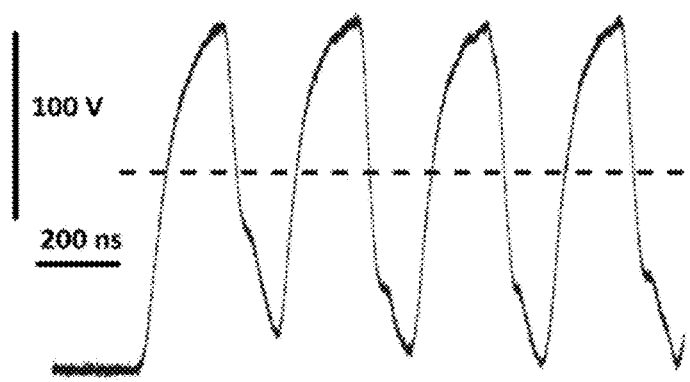
FIGS. 18A-18D a graphs illustrating the viability of EL-4 cells 24 h after exposure to high frequency, sub-microsecond, low electric field bursts.
Figure 18B:
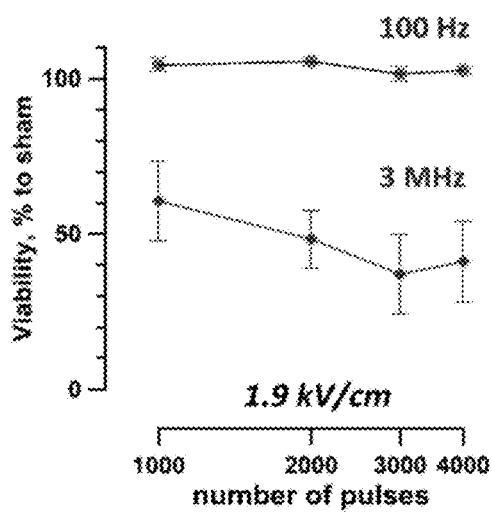
Figure 18C:
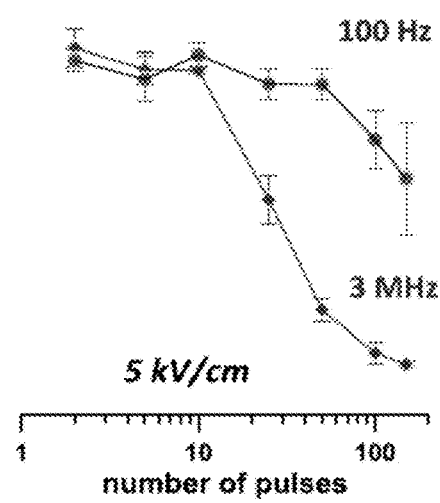

With a low electric field of about 0.64 kV/cm, a burst of 1000, 500-ns pulses caused no permeabilization of HEK cells to either Ca$^{2+}$ ions or YO-PRO-1 below about 0.8-1 MHz (see, e.g., FIGS. 17B-17D). Above this frequency, electropermeabilization steeply increased in this example. The time course and shape of Ca$^{2+}$ transients evoked by MHz bursts (FIG. 17D) and single long pulses (FIG. 17E) were similar, suggesting the same basic mechanism of electroporation. The magnitude of a MHz burst-induced Ca$^{2+}$ response could be matched to that of a single "long" pulse whose duration was made equal to the total time "on" during the burst (not to the total burst duration), as shown in FIG. 17F. The matching condition to evoke the response was found to be:

$$E_{lp}=(E_{nsPEF})\times(\text{duty cycle})+0.05 \qquad [1]$$

where $E_{lp}$ and $E_{nsPEF}$ are, respectively, the electric field values (kV/cm) produced by a long pulse (500 µs) and by sub-microsecond pulses (500 ns) at cell location. Such connection suggested that sub-microsecond bursts and matched single pulses should have comparable physiological consequences, such as the reduction of viability in severely electroporated cells. However, experiments did not confirm this. The viability of EL4 cells electroporated by high frequency, sub-microsecond, low electric field pulsing was also examined. For example, viability experiments of high frequency, sub-microsecond, low electric field pulse treatments of relatively large cell populations in electroporation cuvettes were performed; high frequency, sub-microsecond, low electric field pulse bursts had a triangular shape, with 200 ns width at 50% height, and the applied voltage did not always fully drop to zero between pulses (FIG. 18A). Bursts of 1000 high frequency, sub-microsecond, low electric field pulses were applied at two different peak amplitudes (190 and 500 V, translating into 1.9 and 5 kV in cell suspension), and at low or high repetition rates (100 Hz and 3 MHz). The electric fields of 1.9 kV/cm was below the electroporation threshold for 200-ns pulses applied at 100 Hz, so bursts of up to 4000 pulses did not reduce cell viability. Same pulses applied at 3 MHz were above the threshold and reduced viability about twofold for all tested numbers of pulses (FIG. 18B, p<0.001 compared to 100 Hz, t-test). At about 5 kV/cm, much smaller numbers of pulses reduced viability for both 100 Hz and 3 MHz bursts, but 3 MHz bursts were significantly more efficient (FIG. 18C, p<0.001).

Figure 18D:
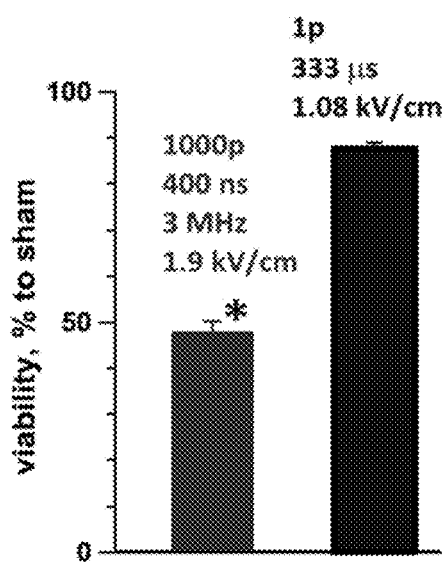

With irregular pulse shape, time-average voltage and electric fields during the burst could not be calculated by multiplying high frequency, sub-microsecond, low electric field pulse amplitude by the duty cycle. Instead, voltages were digitized during a burst with 0.2-ns resolution and calculated their average, which equaled 108 V (1.08 kV/cm) when the peak voltage of high frequency, sub-microsecond, low electric field pulse in the burst was 190 V (1.9 kV/cm). In a separate series of experiments (FIG. 18D), the viability of cells treated by high frequency, sub-microsecond, low electric field pulse bursts (1000 pulses, 400 ns, 3 MHz, 1.9 kV/cm) were compared side by side with single pulses whose duration equaled burst duration (333 µs) and the electric field equaled the time-average value in the burst (1.08 kV/cm). Viability after high frequency, sub-microsecond, low electric field pulse bursts was about 50%, consistent with the previous set (FIG. 17B), whereas an "equivalent" single pulse was significantly less efficient and reduced the viability just to 87.6±1.4%, p<0.0001. Thus, MHz bursts of high frequency, sub-microsecond, low electric field pulse were more efficient than predicted by their time-average amplitude, potentially due to unknown high frequency, sub-microsecond, low electric field pulse specific effects.

These experiments illustrated that excitation and electroporation by high frequency, sub-microsecond, low electric field pulse bursts with up to MHz repetition rates is both effective and efficient. Diverse targets and endpoints all showed increased high frequency, sub-microsecond, low electric field pulse efficiency and decreased the threshold. The efficiency of high frequency, sub-microsecond, low electric field pulse bursts generally increased with the number of pulses per burst, their amplitude, and duty cycle. The efficiency could be significantly different from single long pulses whose duration and amplitude equaled the duration and the time-average amplitude of high frequency, sub-microsecond, low electric field pulse bursts, respectively.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A system for delivery of electrical pulses using megahertz compression to reduce an electrical energy threshold needed to evoke a biological effect, the system comprising:
   a controller;
   an applicator comprising a plurality of electrodes adapted to be placed in proximity to a cell or biological tissue; and
   one or more pulse generators, wherein the one or more pulse generators are each configured to generate a sub-microsecond pulse having a duration of less than 1000 ns,
   wherein the controller is configured to apply, via the applicator, at a frequency equal or greater than 0.1 megahertz (MHz), a first train of sub-microsecond bipolar pulses from a first set of electrodes and a second train of sub-microsecond bipolar pulses from a second set of electrodes, and wherein the first train and the second train are biologically ineffective and configured to result in superposition to create biologically effective unipolar pulses in a region that is remote from the first set of electrodes and the second set of electrodes.

2. The system of claim 1, wherein the controller is configured to apply the first and second trains of sub-microsecond bipolar pulses at a frequency equal or greater than 1 MHz.

3. The system of claim 1, wherein the first and second trains of sub-microsecond bipolar pulses each has a field strength of less than 1 kV/cm.

4. The system of claim 1, wherein the controller is configured to apply the first and second trains of sub-microsecond bipolar pulses wherein the first and second trains of sub-microsecond bipolar pulses each has an electric field strength 800 V/cm or less.

5. The system of claim 1, further wherein the one or more pulse generators comprises a plurality of pulse generators, further wherein the controller is configured to coordinate the plurality of pulse generators to combine sub-microsecond pulses from each of the plurality of pulse generators to form the first and second trains of sub-microsecond bipolar pulses.

6. The system of claim 1, wherein the controller is configured to control the one or more pulse generators so that voltage of the sub-microsecond pulses of the first and second trains of sub-microsecond bipolar pulses is equal or less than 20V.

7. The system of claim 1, wherein the controller is configured to receive one or more user inputs to set or select the frequency of the first and second trains of sub-microsecond bipolar pulses.

8. The system of claim 1, wherein the controller is configured to receive one or more user inputs to set or select voltage of the sub-microsecond pulses of the first and second trains of sub-microsecond bipolar pulses.

9. The system of claim 1, wherein the controller is configured to receive one or more user inputs to select the duration of the sub-microsecond pulses of the first and second trains of sub-microsecond bipolar pulses.

10. The system of claim 1, wherein the plurality of electrodes comprises needle electrodes.

11. The system of claim 1, wherein the applicator is configured to be a hand-held applicator.

12. The system of claim 1, wherein the one or more pulse generators are configured to generate a sub-microsecond pulse having a duration of between 1 ns and 900 ns.

13. The system of claim 1, wherein the controller comprises:
   one or more processors; and
   a machine-readable tangible medium storing a set of instructions for causing the one or more processors to execute operations for:
      delivering a high-frequency, sub-microsecond, pulsed electric field to the biological tissue, wherein the pulsed electric field is pulsed at 0.1 MHz or greater, further wherein each pulse of the pulsed electric field has a duration of less than 1000 ns.

14. The system of claim 13, wherein the set of instructions is further configured to cause the one or more processors to coordinate the one or more pulse generators to generate the high-frequency, sub-microsecond, pulsed electric field.

15. The system of claim 1, wherein the first and second trains of sub-microsecond bipolar pulses each has a field strength of less than 500 V/cm.

16. The system of claim 1, wherein pulses of the first and second trains of sub-microsecond bipolar pulses are damped.

17. The system of claim 1, wherein the controller is configured to control a duty cycle of the first and second trains of sub-microsecond bipolar pulses.

18. The system of claim 1, wherein the applicator is configured to evoke a biological effect of electrical stimulation, poration, or a combination thereof.

19. The system of claim 18, wherein the biological effect is killing the cell or the biological tissue.

20. The system of claim 1, wherein the cell or biological tissue is one or more of: skin, liver, kidney, neuronal, brain, spine, lung, muscle, adipose, respiratory, gastrointestinal, bladder, and reproductive.

21. The system of claim 1, wherein the cell or biological tissue comprises isolated cells.

22. The system of claim 1, wherein the cell or biological tissue comprises a tumor.

23. The system of claim 1, wherein the controller is configured to apply the first and second trains of sub-microsecond bipolar pulses at a frequency equal to 0.5 MHz or greater.

24. The system of claim 1, wherein the second train is phase-shifted relative to the first train.

25. A system for delivery of electrical pulses using megahertz compression to reduce an electrical energy threshold needed to evoke a biological effect, the system comprising:

a controller;

an applicator comprising a plurality of electrodes adapted to be placed in proximity to a cell or biological tissue; and one or more pulse generators, wherein the one or more pulse generators are each configured to generate a sub-microsecond pulse having a duration of less than 1000 ns, wherein the controller is configured to apply, via the applicator, a first train of sub-microsecond bipolar pulses from a first set of electrodes and a second train of sub-microsecond bipolar pulses from a second set of electrodes, wherein the first train and the second train are biologically ineffective and are configured to result in superposition to create biologically effective unipolar pulses in a region that is remote from the first set of electrodes and the second set of electrodes, further wherein the controller is configured to limit a frequency of pulses of the first and second trains of sub-microsecond bipolar pulses to between 0.1 megahertz (MHz) and 100 MHz.

* * * * *